US007369895B2

(12) United States Patent
Hurtado

(10) Patent No.: US 7,369,895 B2
(45) Date of Patent: *May 6, 2008

(54) METHOD FOR APPLYING VARIABLE ELECTRO-MUSCLE STIMULATION AND SYSTEM THEREFOR

(76) Inventor: Arthur F. Hurtado, 7750 Big Rock Dr., Riverside, CA (US) 92509

( * ) Notice: Subject to any disclaimer, the term of this patent is extended or adjusted under 35 U.S.C. 154(b) by 293 days.

This patent is subject to a terminal disclaimer.

(21) Appl. No.: 11/046,496

(22) Filed: Jan. 28, 2005

(65) Prior Publication Data

US 2005/0131488 A1 Jun. 16, 2005

(51) Int. Cl.
*A61N 1/22* (2006.01)

(52) U.S. Cl. .......................... 607/48; 607/77; 607/148; 607/152

(58) Field of Classification Search .................. 607/48, 607/77, 148, 149; 482/1, 92, 140
See application file for complete search history.

(56) References Cited

U.S. PATENT DOCUMENTS

| | | | | |
|---|---|---|---|---|
| 2,764,683 | A * | 9/1956 | De Groff et al. | 331/59 |
| 4,499,900 | A * | 2/1985 | Petrofsky et al. | 607/48 |
| 4,919,148 | A * | 4/1990 | Muccio | 607/152 |
| 4,947,836 | A * | 8/1990 | Laenger et al. | 607/48 |
| 6,341,237 | B1 * | 1/2002 | Hurtado | 607/148 |
| 6,728,577 | B2 * | 4/2004 | Minogue et al. | 607/48 |
| 6,760,629 | B2 | 7/2004 | Minogue et al. | |
| 6,876,883 | B2 * | 4/2005 | Hurtado | 607/48 |
| 6,885,896 | B2 | 4/2005 | Minogue et al. | |
| 7,069,089 | B2 | 6/2006 | Minogue et al. | |
| 2006/0206168 | A1 | 9/2006 | Minogue et al. | |

* cited by examiner

*Primary Examiner*—Mark Bockelman

(57) ABSTRACT

A method for applying variable electro-muscle stimulation (EMS) to an exercising person includes a belt having a plurality of electrodes placed around the abdomen at the rectus abdominis and obliques. The person then gets into an exercise apparatus which has a rotatable component. Attached to the rotatable component is a transducer that senses the position of the component. An EMS generator is connected to the belt through the transducer. As the user exercises in a first direction, increasing stimulation is applied to the subject muscles. As the user moves the rotatable component in the opposite direction, decreasing stimulation is applied to the user. In an alternative embodiment, the belt has at least one pair of electrodes connected to a common adjustment control so that as the voltage increases to one of the electrodes, it decreases to the other electrode of the pair, and vice versa. A toggle switch makes possible the selection of a particular pair.

10 Claims, 18 Drawing Sheets

METHOD FOR APPLYING VARIABLE ELECTRO-MUSCLE STIMULATION AND SYSTEM THEREFOR

CROSS REFERENCE TO RELATED APPLICATION

This application claims the filing benefit under 35 U.S.C. §120 of U.S. Utility Patent Application No. 10/348,879, filed Jan. 21, 2003, now U.S. Pat. No. 6, 876,833, issued Apr. 5, 2005, and under 35 U.S.C. §119(e) of U.S. Provisional Application No. 60/405,659, filed Aug. 26, 2002, which are included herein by reference.

TECHNICAL FIELD

The present invention pertains generally to electro-muscle stimulation (EMS), and more particularly to a method and system for applying a varying level of EMS as a user activates an exercise apparatus.

BACKGROUND OF THE INVENTION

Electro-muscle stimulation (EMS) is well known in the medical art. This technology utilizes a conductive pad or electrode to externally apply a very weak current to a muscle or group of muscles and thereby cause them to contract. The electrode receives an electric stimulation signal from an external voltage/current source, such as an EMS machine. The stimulation signal can be adjusted in amplitude, polarity, frequency, waveform, etc. EMS is commonly used in physical or occupational therapy to strengthen atrophied muscles or paralyzed limbs. It is also used to exercise muscles that are immobilized for long periods of time as a result of muscular or neurological disorders, or extended periods of bed rest arising from injury, surgery, or illness. EMS is also useful for the general exercise of functional muscles to improve muscle tone and strength. For example, athletes can use EMS to treat muscle injuries as a supplement to conventional conditioning exercises. EMS can also be used to recondition muscles or muscle groups which have, for whatever reason, lost their tone and/or strength, have been injured, or are in need of reconditioning to effect cosmetic improvements. An operator who has been trained in the principles of EMS can analyze the areas which are of concern and select the proper muscles to exercise and train.

For example, U.S. Pat. No. 6,341,237 illustrates a device for administrating EMS which includes a flexible covering having a plurality of spaced apart electrodes. In a preferred embodiment, the flexible covering is shaped like a band or belt, and is designed to encircle and be connected around a portion of a patient's body. The band or belt is fabricated from an elastic material so that the electrodes are pressed against the skin of the patient to promote better electrical conduction. Electrodes are selectively positionable to different locations on the flexible covering so they may be placed directly over a selected muscle or muscle group. Each electrode has its individual control for adjusting the level of the electrical stimulation signal so that different muscles can receive different levels of stimulation and the level of stimulation may be changed during the course of treatment. A master adjustment control can be used to adjust the stimulation signal level applied to all electrodes. In a preferred embodiment, the individual adjustment controls are located adjacent their respective electrodes on the flexible covering. U.S. Pat. No. 4,480,830 illustrates a method and apparatus for exercising paralyzed muscles. The method and apparatus make use of a set of transcutaneous electrodes which are placed upon the skin of the subject over muscles which are to be stimulated. A computer controlled stimulator generates a pair of alternately pulsed stimulation signals which are applied across different pairs of stimulation electrodes to produce controlled muscle contraction. Muscle movement is resisted by a dynamic load and a position sensor provides a feedback signal indicating the movement actually achieved. The computer uses the feedback signal for modifying the control signal applied to the stimulator. U.S. Pat. No. 4,499,990 shows a system and method for treating persons with paralyzed legs. The apparatus and method include four sets of transcutaneous electrodes which are placed above the iliac and quadriceps muscles of the paralyzed person. The person is seated upon an exercycle and a series of pulsed stimulation signals are applied to the electrodes to cause coordinated contraction of the iliac and quadriceps muscles. This causes pedaling of the exercycle by the paralyzed legs. A position sensor senses the position of the pedals and transmits an indication thereof to a computer which generates control signals for stimulation driving circuits connected to the stimulation electrodes. U.S. Pat. No. 4,586,495 illustrates an apparatus and method for stimulating muscular activity in an acutely injured patient. A leg which is to be stimulated is strapped into a brace and the leg muscles are stimulated to work isometrically against the brace. The effort exerted by the muscles is measured by load cells which generate feedback signals for a control computer. The computer adjusts the stimulation signals in accordance with the received feedback signals. U.S. Pat. No. 4,586,510 discloses an apparatus for exercising a paralyzed limb by functional electrical stimulation. The system utilizes simple analog devices including a reference signal generator, a position sensor, and an error signal generator. The error signal is integrated to produce a stimulation driving signal for application to the stimulation electrodes mounted on the limb. In the disclosed embodiment, the paralyzed person may be seated in an exercise chair which is equipped with a pair of loading assemblies which are attachable to the legs of the person so as to yieldingly resist the stimulated movement. U.S. Pat. No. 4,724,842 shows a method and apparatus for muscle stimulation. An exercise machine or dynamometer is provided with control apparatus for ascertaining the physical position of a patient during an exercise. The patient is then electrically stimulated over selected ranges of motion in order to aid in the exercise. U.S. Pat. No. 5,070,873 includes a method of and apparatus for electrically stimulating quadriceps muscles of an upper motor unit paraplegic. Muscle fatigue of an electrically stimulated quadriceps muscle of an upper motor neuron paraplegic is detected and compensated for by monitoring the myoelectric (EMG) signal produced by the stimulated muscle and controlling one or more of the following parameters of the electrical stimulation (ES) signal: pulse repetition rate, amplitude, and pulse width. U.S. Pat. No. 5,507,788 illustrates a method and apparatus for controlling skeletal muscle fatigue during electrical stimulation. Electrical stimulation signals are applied to muscles at a frequency which is varied in response to a detected ripple signal in an output tension or torque record which corresponds to the fusion of the multiple muscle contractions. An average torque amplitude is first determined when a stimulation signal is applied at an initial frequency. The amplitude of the ripple on the torque output is then determined and compared to the average torque amplitude to provide a ripple percentage. The measured ripple percentage is compared to a selected ripple percentage corresponding to the desired fusion of the multiple muscle contractions. And the stimulation frequency is adjusted by a feedback loop until the measured ripple percentage conforms to the selected value. U.S. Pat. No. 5,628,722 shows a method for maintaining knee stability of a user suffering from damage to a knee ligament. The method includes a sensor feedback system for measuring abnormal physical relationships between the tibia and femur. The sensor feedback system determines whether selected conditions have been met warranting the application of electrical stimulation and provides information regarding the determination to an electronic stimulator. Electrodes are spaceably mounted on the hamstring and/or quadriceps muscles in electrical communication with the electronic stimulator for causing contraction of the thigh muscles at selected levels, thus providing a posteriorly and/or anteriorly directed force to the upper tibial bone and thereby preventing its instability.

SUMMARY OF THE INVENTION

The present invention is directed to a method and associated system for applying varying electro-muscle stimulation. The method can be practiced on any exercise apparatus which has a rotational element upon which the user exerts a force during the course of exercising. A transducer senses the rotation of the exercise apparatus, and delivers an output signal to an EMS covering such as a belt which is placed on a target muscle group of the user. As the user works to rotate the apparatus, the output signal of the transducer increases from zero at no rotation to a maximum value as a function of the amount of rotation. In this fashion the electro-muscle stimulation rises smoothly as the muscle moves during flexion and peaks upon full contraction or end phase of motion.

A preferred name for the present invention is electro-augmented myociser. The electro-augmented myociser is to be used concurrently with an electro myociser belt, which consists of a belt having electrodes strategically placed to stimulate specific muscles of the body. Electrical signals, directed by the location of the electrodes within the belt, are emitted causing contraction of targeted muscles.

The purpose of the electro-augmented myociser is to augment and enhance natural exercise by encouraging maximum muscle contraction of those muscles that are easily exercised. It also isolates and enhances contraction of targeted muscle groups that are difficult to exercise. Controls allow the user to establish the level of difficulty that is comfortable and change the level during use. Additionally, the user may change the stimulus to specific sites within a muscle group during use.

The present invention may be incorporated in a vast variety of exercise apparatus including but not limited to equipment used to exercise the abdomen, deltoids, biceps, hamstrings, and quadriceps. It operates under the principle of voltage application being supplied only as the person contracts or actuates his or her muscles. As the person exercises activating a range of motion, the exercise apparatus moves or pivots. The movement or rotation of the equipment is mechanically coupled to a transducer that controls the output of the electrical stimulus. The voltage rises smoothly as the muscle moves causing contraction to peak upon full contraction. In the opposite direction, the voltage reduces smoothly as the muscle is relaxed. When the muscle is at rest, or fully elongated, the voltage is zero. In the process of performing active exercise with augmented electro muscle stimulation, the tendons and bones realize a healthier benefit than merely administering passive muscle stimulus alone. What is completely unique about the present invention is that the voltage surge is not controlled by the machine, but is instead controlled by the actions of the individual performing the exercise. The present invention will further induce motivation by enabling the person to perform a greater number of repetitions with less effort, thereby providing enhanced muscle development in a shorter time span.

Alternately, the user may have the option of putting the electrical stimulation from the voltage source to the belt on automatic to a predesignated mode and rate when he becomes fatigued and unable to continue exercising. The preferred mode is a surge mode. For example, a surge of eight seconds on and five seconds off may be selected. This provides a constricting action on the abdominals with a rest or recovery period. The surge mode tends to give a better result than using a pulse mode.

In accordance with a preferred embodiment of the invention, a method for applying variable electro-muscle stimulation, includes:

(a) providing a flexible electro-muscle stimulation covering having a plurality of spaced apart electrodes, the electrodes disposed in a pattern upon the flexible covering which matches a predetermined group of human muscles, so that when the flexible covering is placed upon a patient, the electrodes are proximate to the predetermined group of muscles, wherein the pattern matches predetermined groups of muscles, the muscles being the upper portion of the rectus abdominus, the lower portion of the rectus abdominus, the right obliques, and the left obliques.

(b) providing an exercise system having (1) an exercise apparatus having a member which is rotatable about an axis by an exercising user, and (2) a transducer communicating with the axis, so that as the member is rotated, the transducer generates an output signal which is a function of an angular position of the member;

(c) providing an electro-muscle stimulation system which delivers a voltage to the transducer;

(d) providing electrical emphasis to certain regions over other regions within the muscle group;

(e) placing the electro-muscle stimulation covering upon a target muscle group of the user;

(f) causing the output signal to be delivered to the electro-muscle stimulation covering;

(g) the user rotating the member in a first direction thereby causing the output signal to increase thereby causing increased electro-muscle stimulation to be applied to the user; and, (h) the user rotating the member in an opposite direction thereby causing the output signal to decrease thereby causing decreased electro-muscle stimulation to be applied to the user.

In accordance with another preferred embodiment of the invention, a method for applying variable electro-muscle stimulation, includes:

(a) providing an electro-muscle stimulation device having:

- a flexible covering having a plurality of spaced apart electrodes;
- the electrodes including:
  - a first positive electrode;
  - a second positive electrode; and,
  - a return electrode disposed between the first and second positive electrodes;
- a voltage source connected between the positive electrodes and the return electrode; and, an adjustment control which simultaneously applies a first positive voltage to the first positive electrode and a second positive voltage to the second positive electrode, so that as the first positive voltage increases, the second positive voltage decreases, and as the first positive voltage decreases, the second positive voltage increases;

(b) providing an exercise system having:

an exercise apparatus having a member which is rotatable about an axis by an exercising user;

a transducer communicating with the axis; and, so that as the member is rotated, the transducer generates an output signal which is a function of an angular position of the member;

(c) providing an electro-muscle stimulation system which delivers a voltage to the transducer;

(d) placing the electro-muscle stimulation covering upon the user;

(e) causing the output signal to be delivered to the electro-muscle stimulation covering;

(f) the user rotating the member in a first direction thereby causing the output signal to increase thereby causing increased electro-muscle stimulation to be applied to the user; and, (g) the user rotating the member in an opposite second direction, thereby causing the output signal to decrease thereby causing decreased electro-muscle stimulation to be applied to the user.

Other aspects of the present invention will become apparent from the following detailed description, taken in conjunction with the accompanying drawings, which illustrate, by way of example, the principles of the invention.

DETAILED DESCRIPTION OF THE INVENTION

Figure 1:
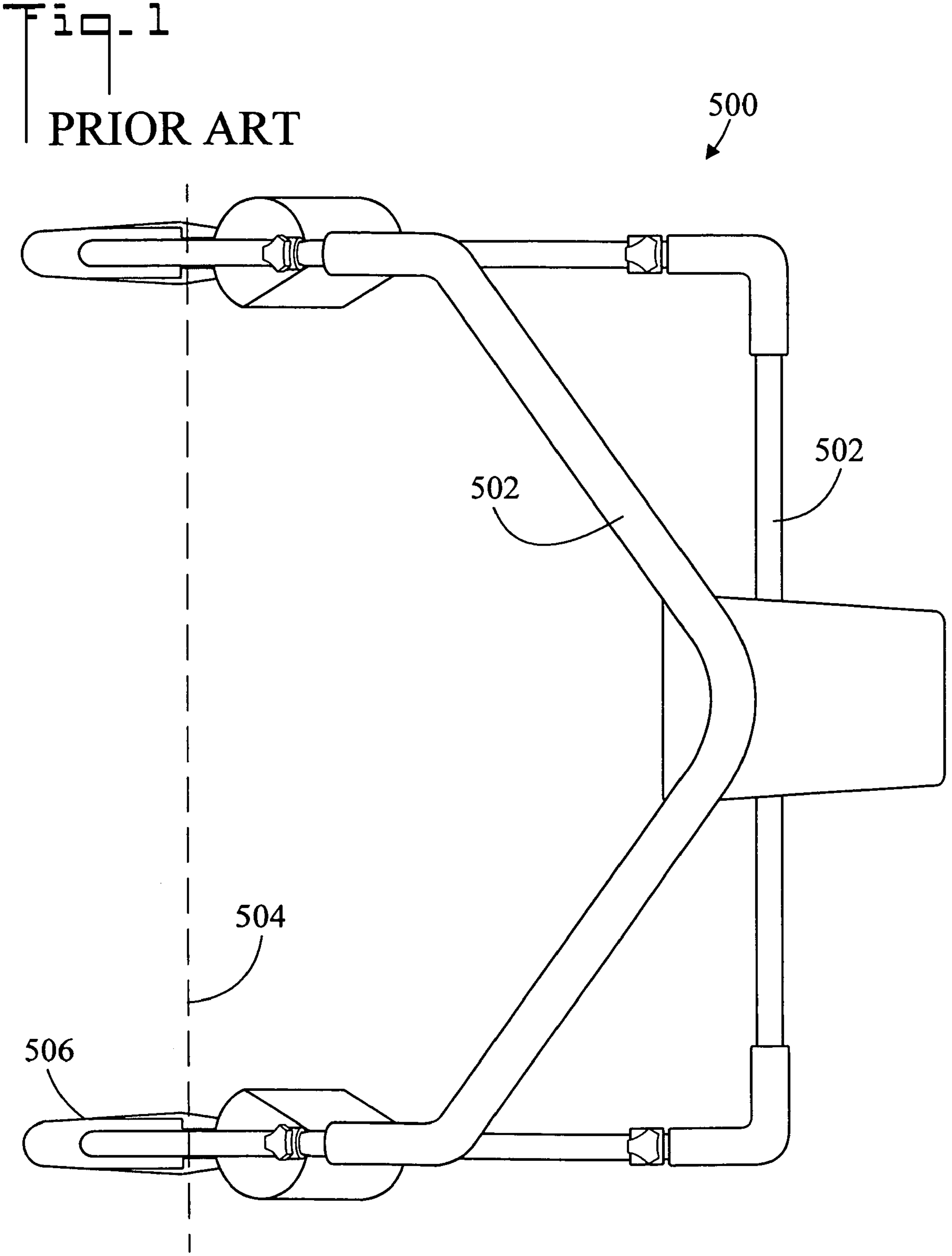
FIG. 1 is a top plan view of a prior art exercise apparatus.
Figure 2:
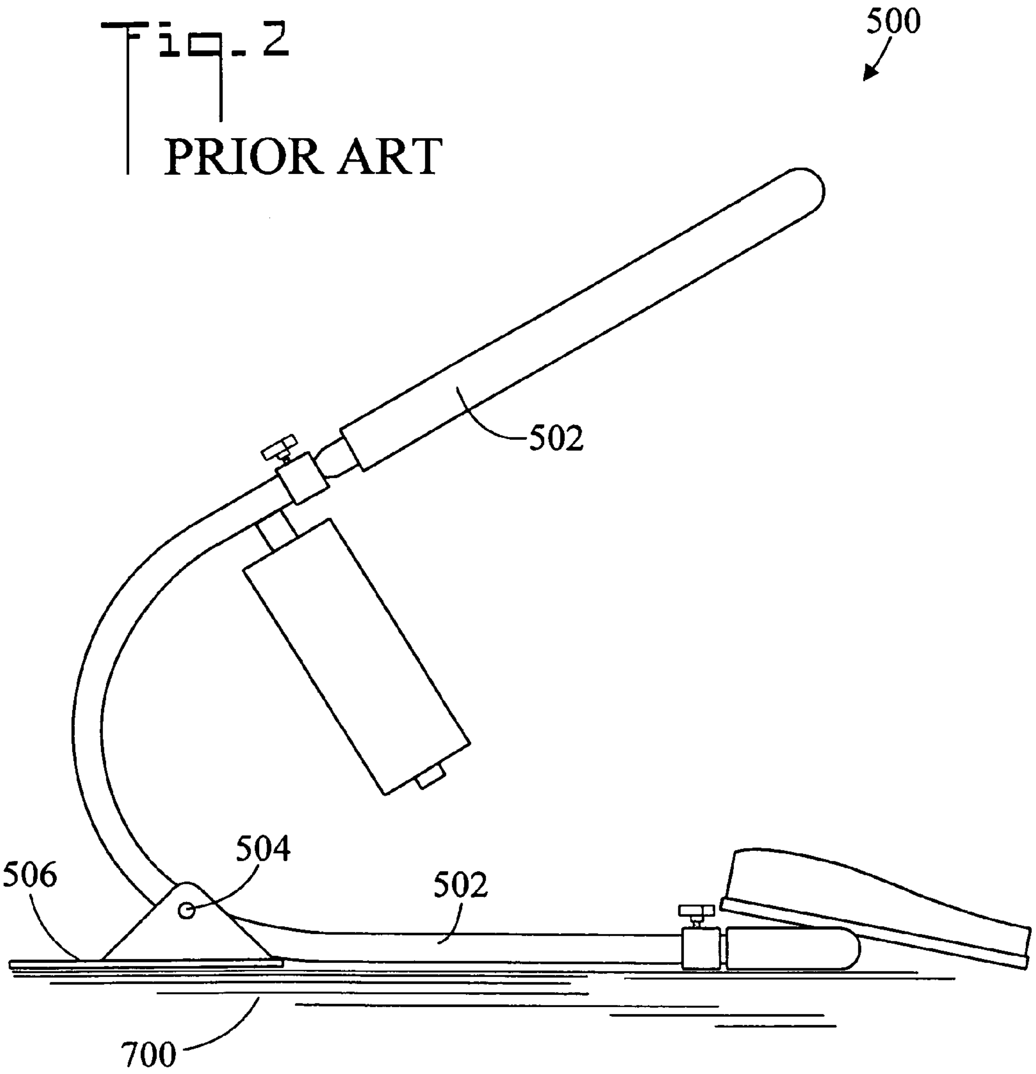
FIG. 2 is a side elevation view of the prior art exercise apparatus.

FIGS. 1 and 2 are top plan and side elevation views, respectively, of a prior art exercise apparatus, generally designated as 500. In the shown embodiment, exercise apparatus 500 comprises an abdominal roller which is used to exercise the abdominal muscles of an exercising user. Exercise apparatus 500 includes a member 502 which is rotatable about an axis 504 such as an axle by the exercising user. Member 502 rotates about base 506 which resides on a support surface 700.

Figure 3:
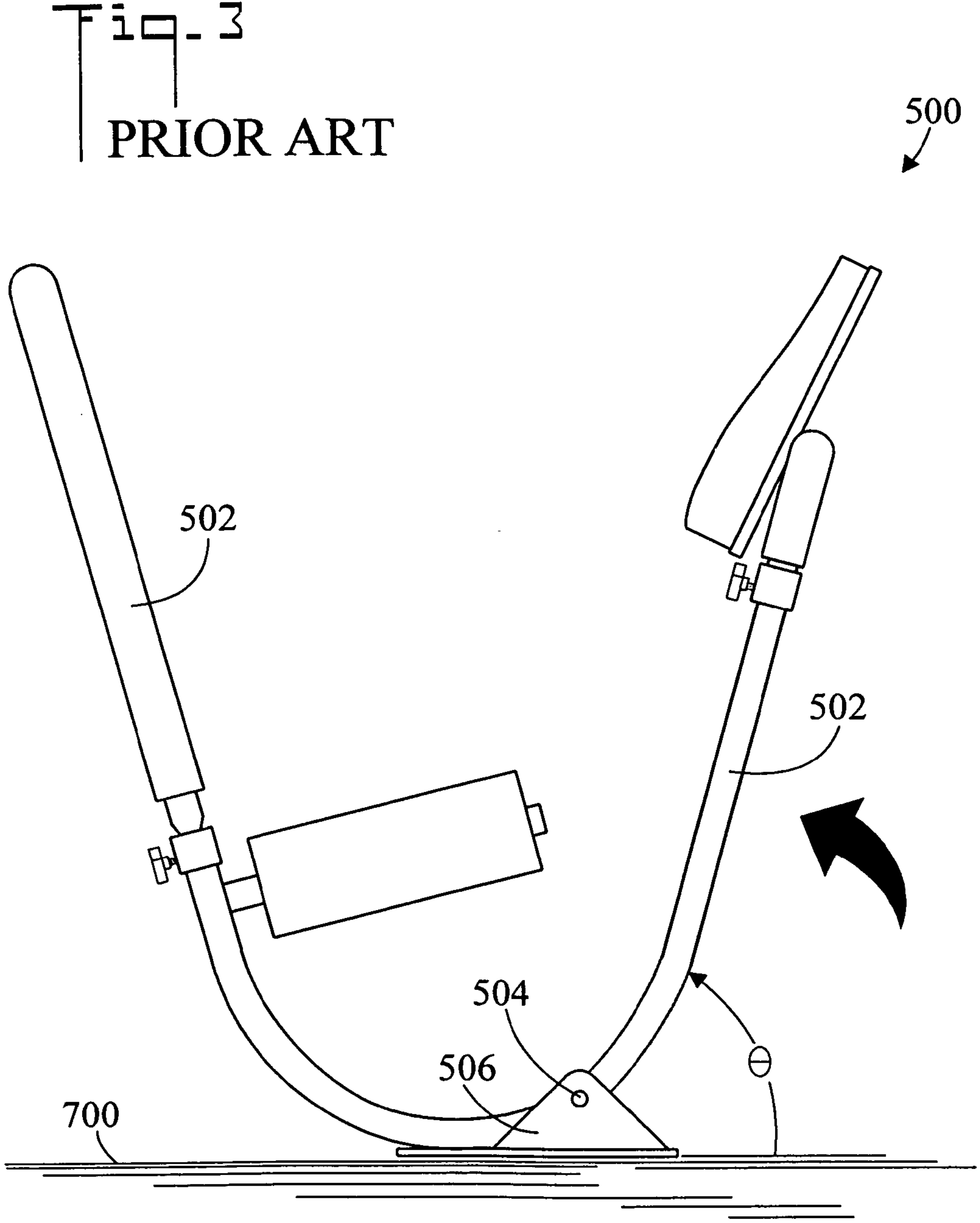
FIG. 3 is a side elevation view of the prior art exercise apparatus rotated to a second position.

FIG. 3 is a side elevation view of prior art exercise apparatus 500 rotated through an angle θ to a second position.

Figure 4:
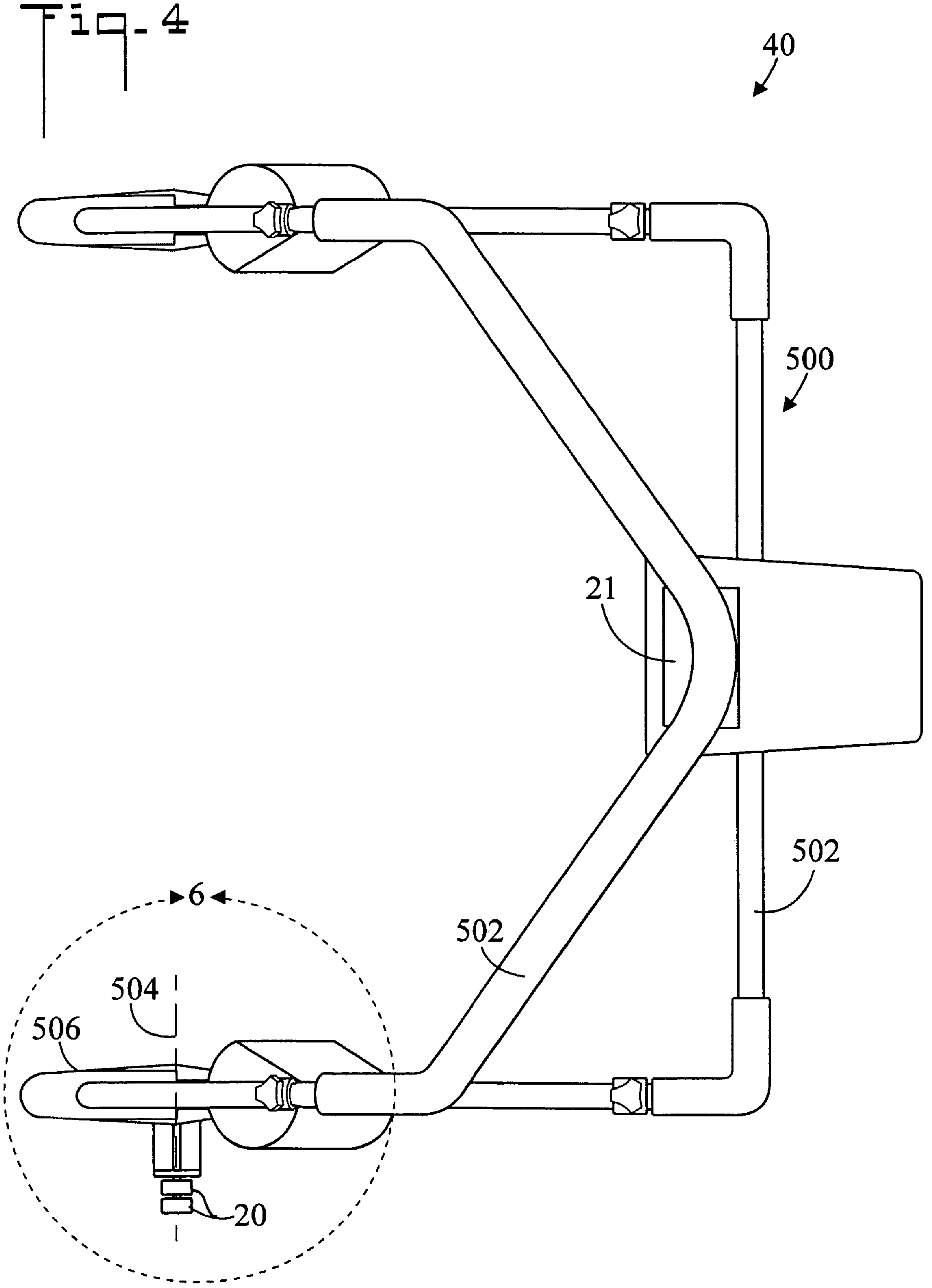
FIG. 4 is a top plan view of a system for applying electro-muscle stimulation in accordance with the present invention.
Figure 5:
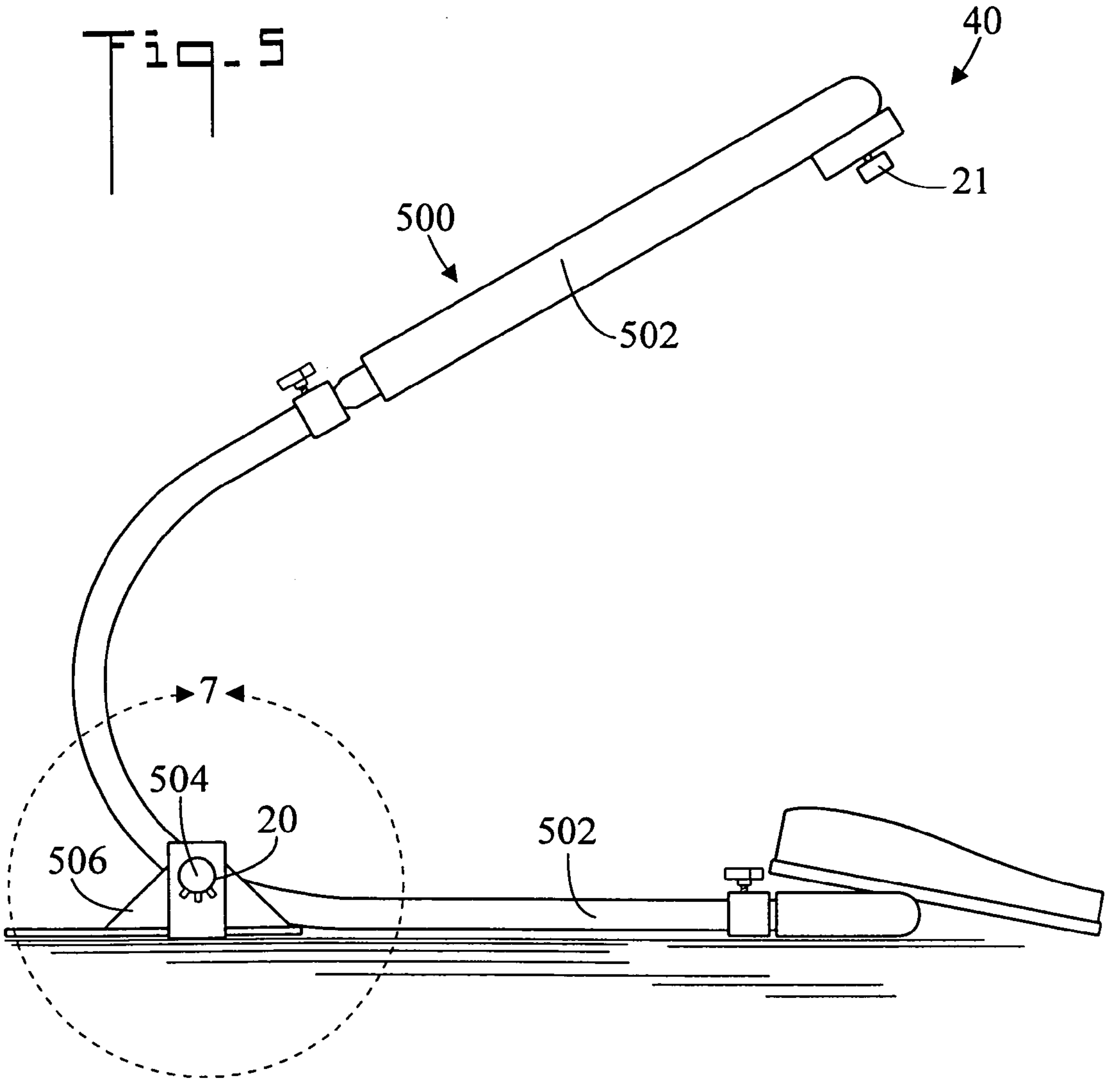
FIG. 5 is a side elevation view of the system.

FIGS. 4 and 5 illustrate top plan and side elevation views, respectively, of a system for applying variable electro-muscle stimulation in accordance with the present invention, generally designated as 40. System 40 includes exercise apparatus 500 having a member 502 which is rotated about an axis 504 by an exercising user. A transducer 20 communicates with axis 504, so that as member 502 is rotated about axis 504, transducer 20 generates an output signal which is a function of an angular position of member 502.

Figure 6:
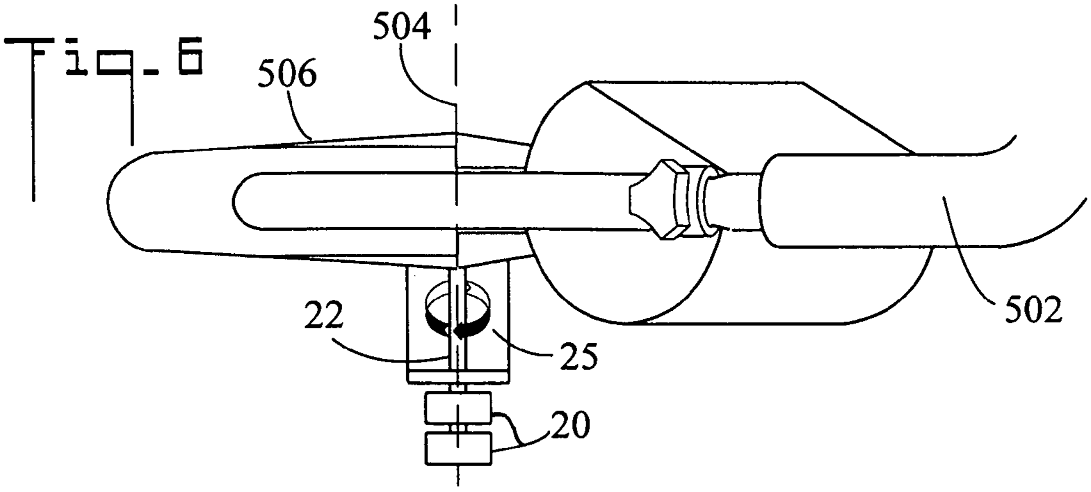
FIG. 6 is an enlarged view of area 6-6 of FIG. 4.

FIG. 6 is an enlarged view of area 6-6 of FIG. 4. In the shown embodiment, transducer 20 is an angular position-to-voltage transducer, such as a potentiometer. Transducer 20 is connected by shaft 22 to axis of rotation 504 of member 502, so that as member 502 is rotated, shaft 22 of transducer 20 also rotates. The housing of transducer 20 is attached to a bracket 25 which is in turn attached to base 506. In this manner, as member 502 is rotated about axis of rotation 504, shaft 22 rotates and changes the output signal $V_\theta$ of transducer 20 (refer also to FIG. 9). It is noted that a plurality of transducers 20 may communicate with axis 504, such as the two shown in the FIG. 6. It may be appreciated that other shaft position transducers such as shaft angle encoders, digitizers, etc. could be utilized to convert the rotation of member 502 into an output signal.

Figure 7:
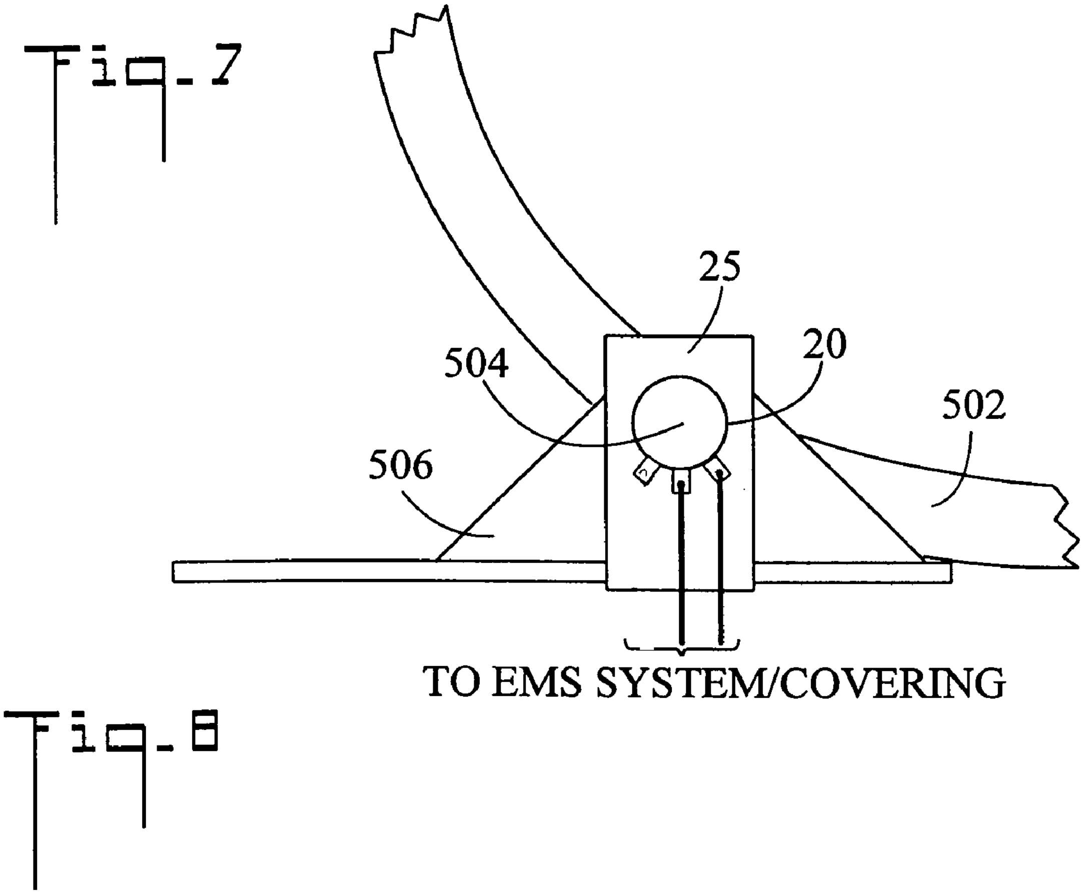
FIG. 7 is an enlarged view of area 7-7 of FIG. 5.

FIG. 7 is an enlarged view of the area 7-7 of FIG. 5. It is noted that the terminals of transducer 20 are routed to an EMS system (machine) and an EMS covering which is placed upon an appropriate part of the exercising user's body (refer also to FIGS. 8, 10, and 11).

Figure 8:
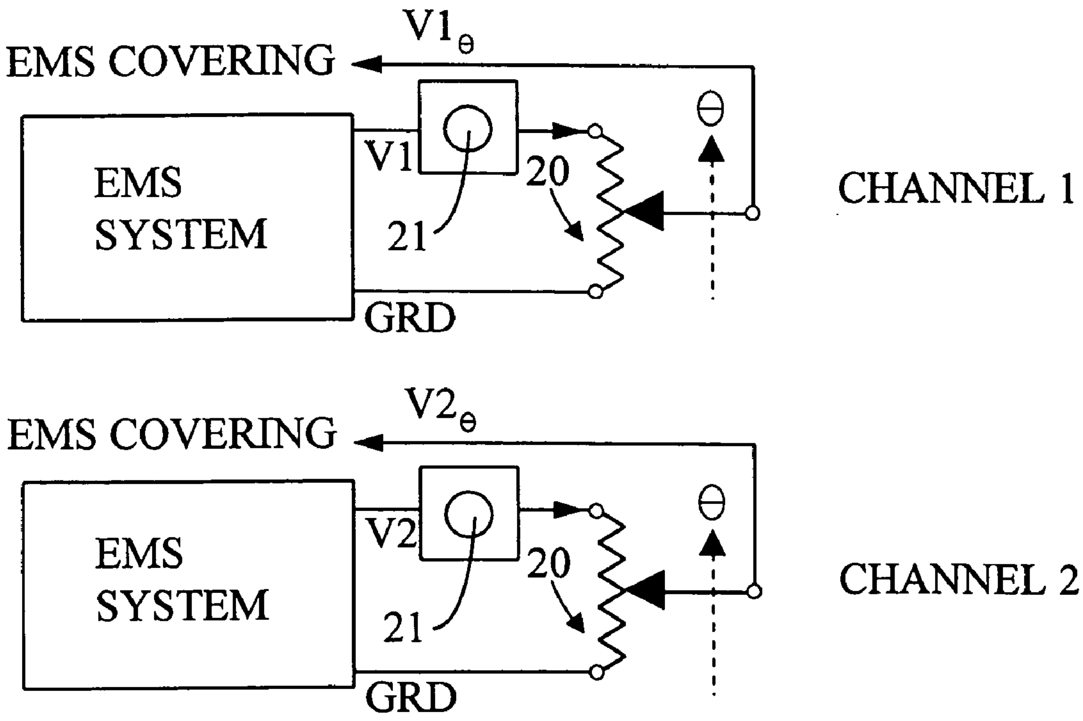
FIG. 8 is an electrical schematic diagram of the present invention.

FIG. 8 is an electrical schematic diagram of the present invention. An EMS system delivers a voltage V1 to transducer 20. In the shown embodiment voltage V1 is referenced to ground, however other reference arrangements are also possible. As member 502 of exercise apparatus 500 is rotated through angle θ, the wiper of transducer 20 generates an output signal (voltage $V1_\theta$) which is routed to an EMS covering such as a belt which is placed upon a part of the user's body (refer to EMS covering 550 in FIGS. 10 and 11).

Output signal $V1_\theta$ increases from a minimum value for θ=zero, to a value of V1 for θ=a maximum rotational value. In the shown embodiment, two transducers 20 comprise two separate channel inputs (1 and 2) to the EMS covering. In one embodiment, the two channels deliver EMS to different muscle groups of the user. In an embodiment of the invention, a voltage level control 21 is provided on each of the two channels. The voltage level control 21 includes a potentiometer which controls the voltage (V1 or V2) delivered to transducer 20, and thereby the intensity of the electro-muscle stimulation. The mechanical placement of the voltage level control 21 is shown in FIGS. 4, 5, 10, 11, and 20-23. The voltage level control is placed so a user can conveniently control the intensity of the EMS during exercise without breaking the exercise rhythm.

Figure 9:
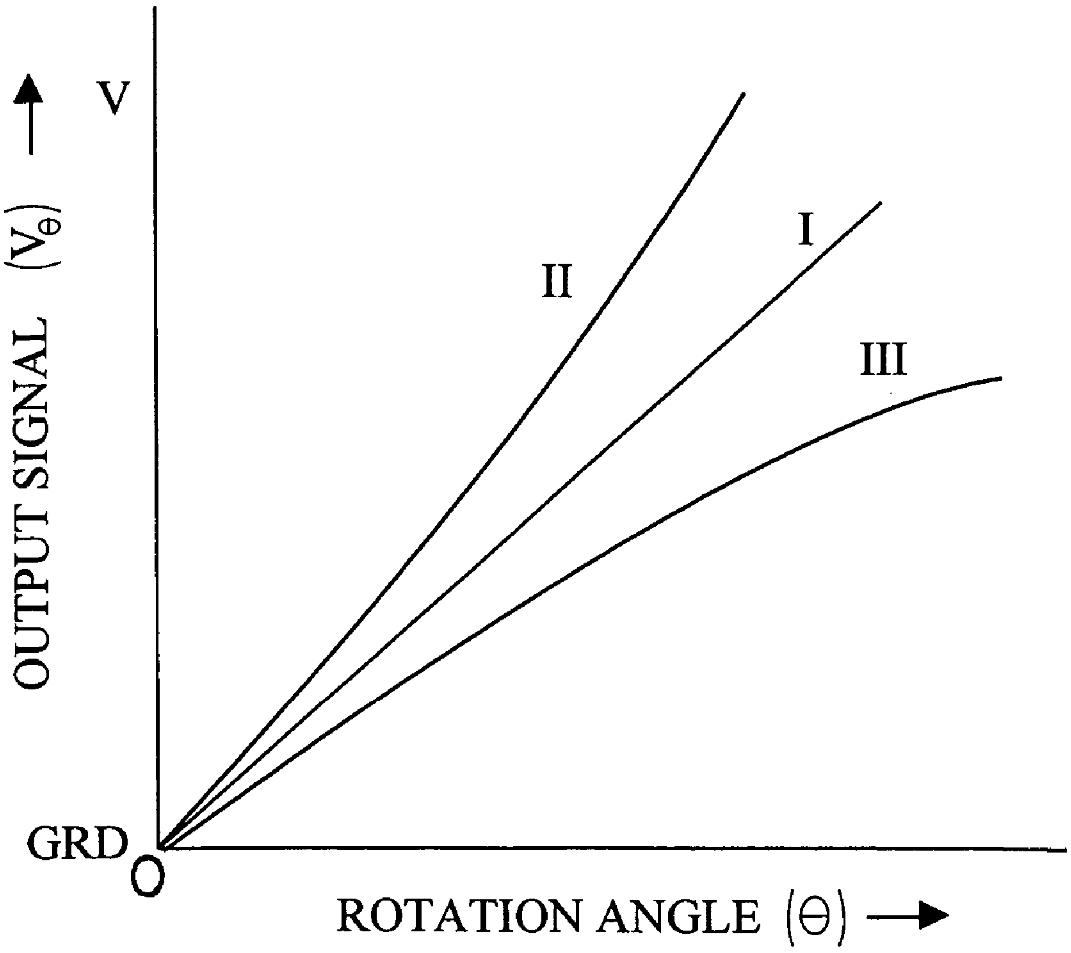
FIG. 9 is a graph which illustrates an output signal $V_\theta$ as a function of rotational angle θ.

FIG. 9 is a graph which illustrates the output signal $V_\theta$ as a function of rotational angle θ of member 502. The output signal $V_\theta$ rises smoothly as the exercise apparatus 500 is rotated. The output signal $V_\theta$ could be linear as shown in I, or nonlinear as shown in II or III.

Figure 10:
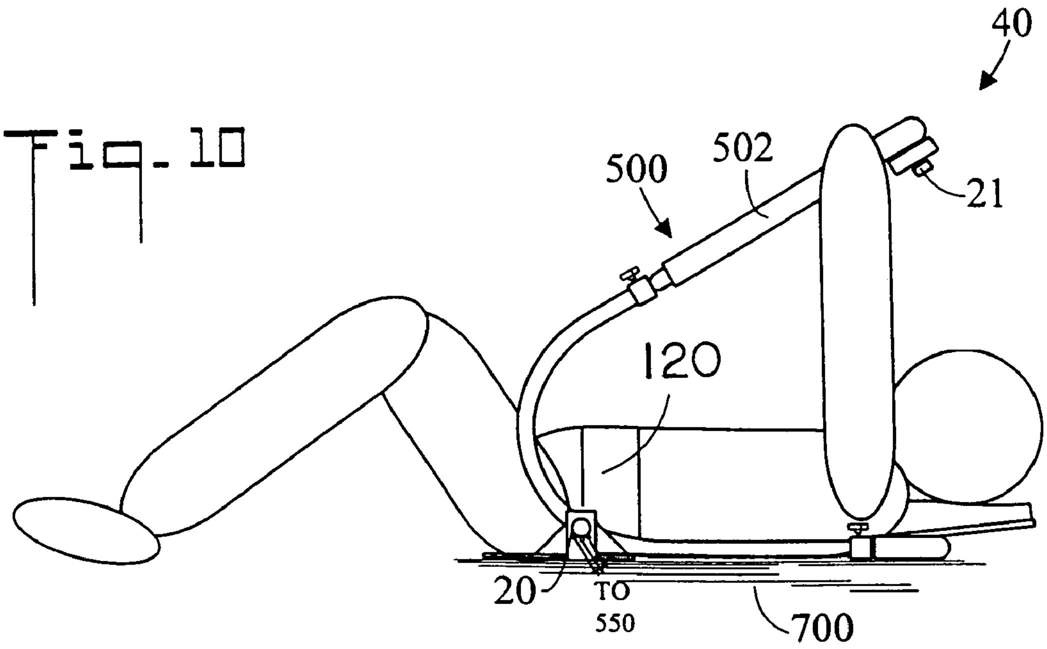
FIG. 10 is a reduced side elevation view of the system of the present invention being used by an exercising user in an initial position.
Figure 11:
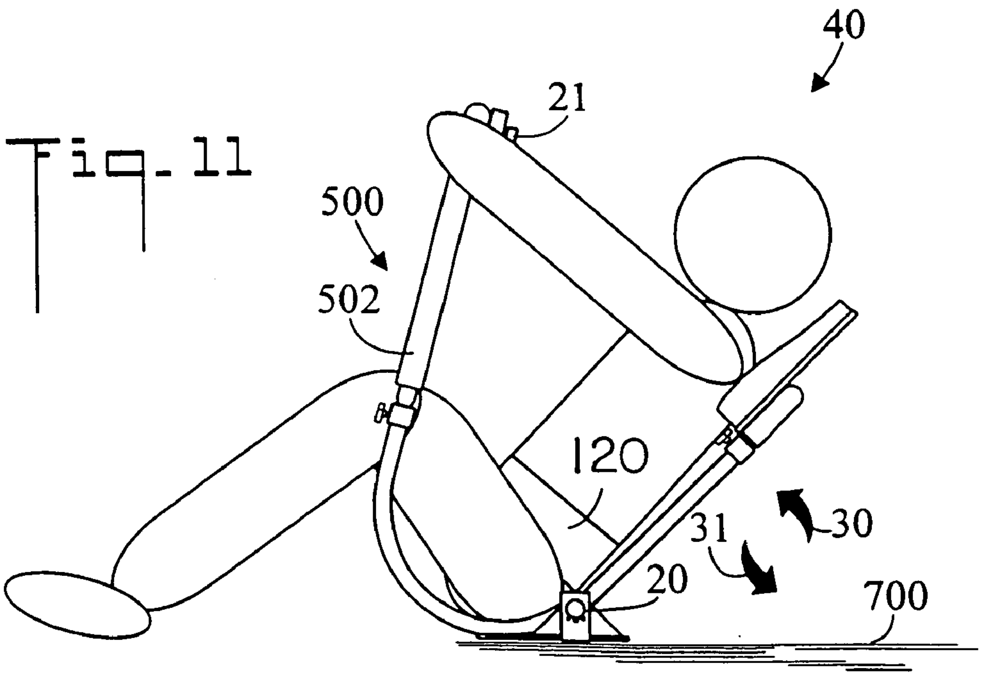
FIG. 11 is a reduced side elevation view of the system of the present invention being used by an exercising user in a rotated position.

FIGS. 10 and 11 are side elevation views of system 40 being used by an exercising user. In FIG. 10 the user is initially reclining on his or her back, and in FIG. 11 the user has rotated to the shown position. An EMS covering 120 is disposed around the user's abdomen. The output signal $V_\theta$ from transducer 20 is delivered to the EMS covering 120. As the user rotates member 502 from the position of FIG. 10 in a first direction 30, output signal $V_\theta$ increases thereby causing increasing electro-muscle stimulation. Conversely, as the user rotates member 502 in an opposite second direction 31, output signal $V_\theta$ decreases thereby causing decreasing electro-muscle stimulation. It is noted that the output signal $V_\theta$ increases as the user is using his or her abdominal muscles to rotate member 502. Applying increasing electro-muscle stimulation as the user is using his or her muscles, enhances the benefits of the exercise. Voltage level control 21 is conveniently located on member 502 adjacent the hands of the user so that the intensity of the EMS can be adjusted during exercise without breaking the exercise rhythm.

Figure 12:
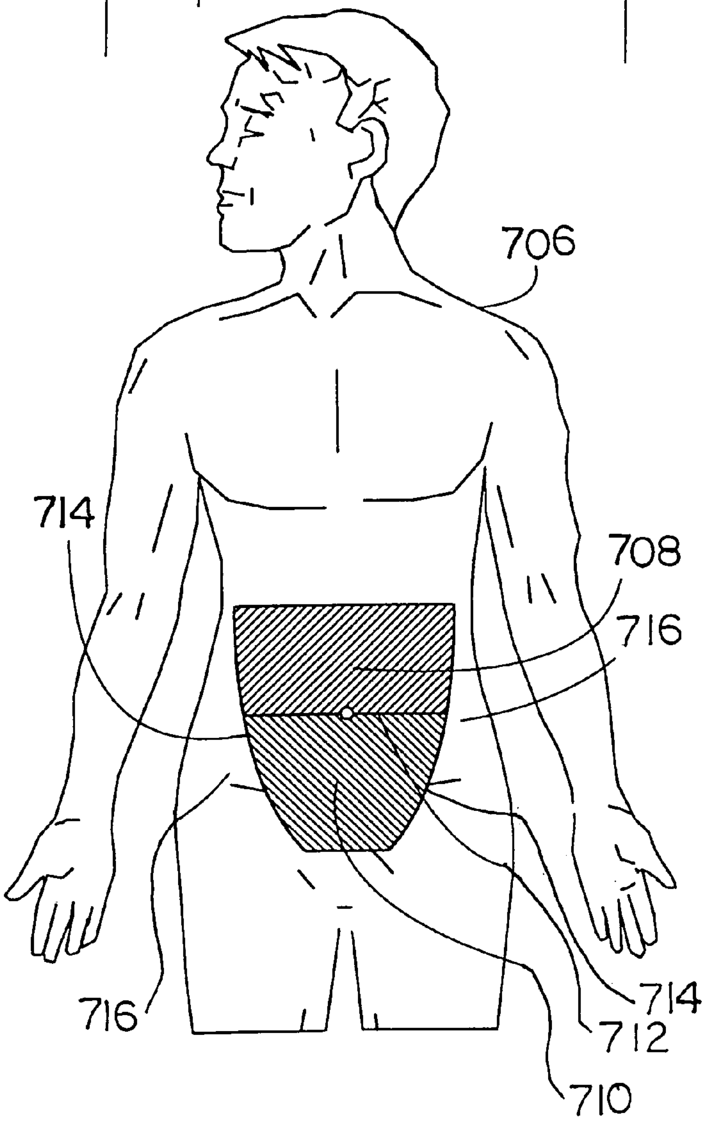
FIG. 12 is a front elevation view of a user.

FIG. 12 is a front elevation view of a patient 706 showing the muscles of the rectus abdominis divided at the umbilical area 712 into an upper portion 708 and a lower portion 710. The rectus abdominis includes two distinct muscles on opposite sides of the linea alba. But for purposes of this invention, they work together and are stimulated together. Line 714 defines the junction of the right and left obliques 716 with the upper portion 708 and lower portion 710 of the rectus abdominis (refer also to FIG. 13).

Figure 13:
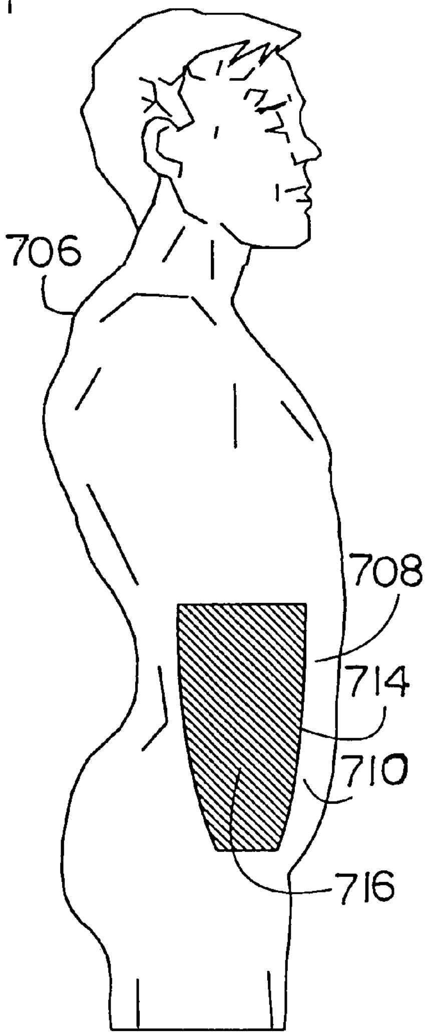
FIG. 13 is a side elevation view of a user.

FIG. 13 is a side elevation view of the patient 706 showing the right obliques 716. The left obliques are on the opposite side. Line 714 defines the junction of the right obliques 716 with the upper portion 708 and lower portion 710 of the rectus abdominis.

Figure 14:
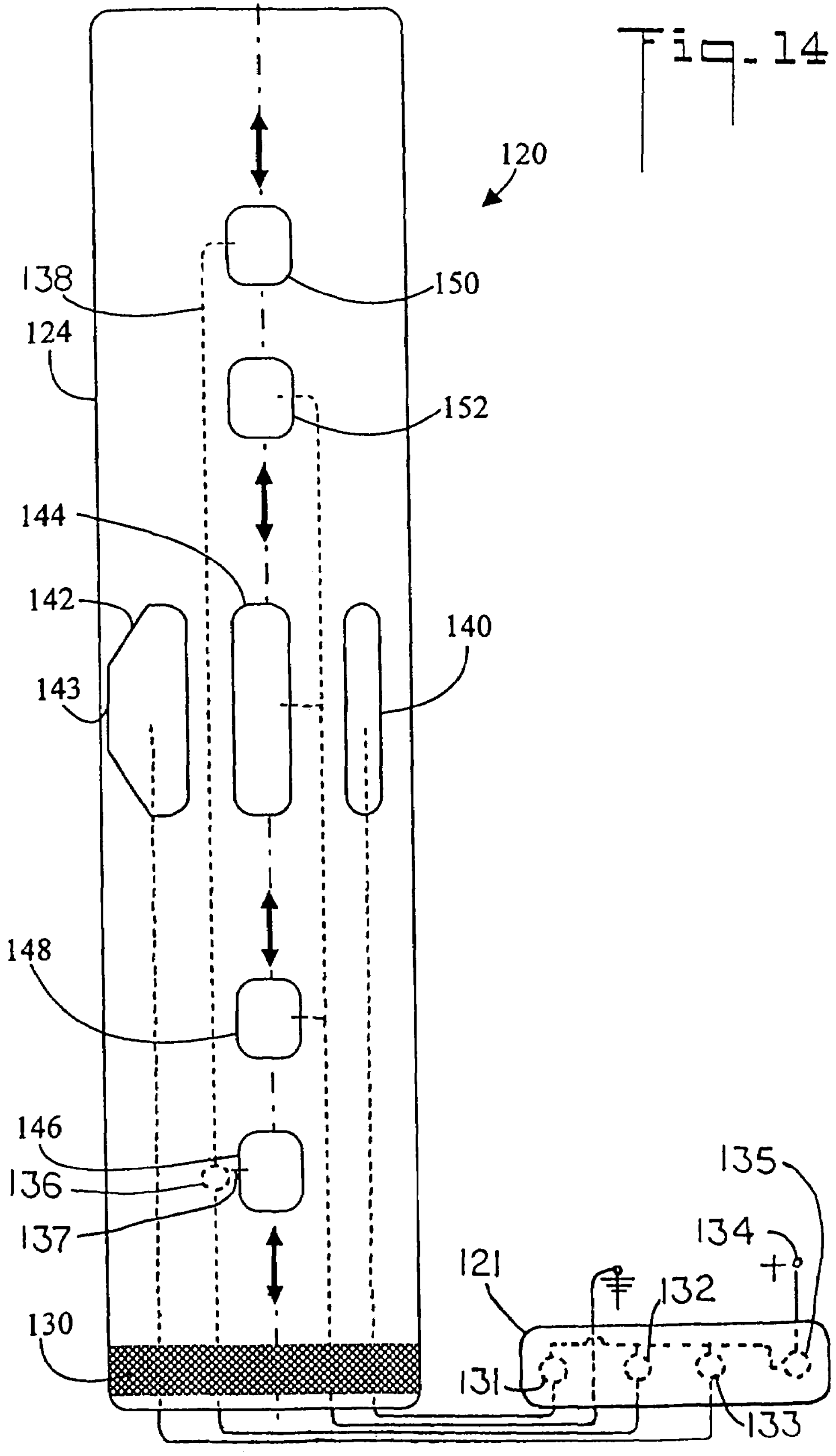
FIG. 14 is a top plan view of the outside of an abdominal covering.

FIG. 14 illustrates a top plan view of the outside of the abdominal covering 120 of FIGS. 10 and 11. The abdominal covering or belt is specifically designed to encircle the abdomen and stimulate the muscle groups of the central torso. Abdominal covering 120 includes a flexible covering or band 124, selectively positionable electrodes 146, 148, 150, and 152, and connector 130. The stimulated muscles (FIGS. 12 and 13) are the upper portion 708 and the lower portion 710 of the rectus abdominis, the right obliques 716, and the left obliques. Abdominal covering 120 includes a first positive electrode 140 which, when placed upon a patient, is proximate to the upper portion 708 of the rectus abdominis, a second positive electrode 142 which, when placed upon a patient, is proximate to the lower portion of the rectus abdominis, and a third negative return or common electrode 144 disposed between first 140 and second 142 positive electrodes in the umbilical region 712. Return electrode 144 provides a conduction path for both first positive electrode 140 and second positive electrode 142. It is noted that second positive electrode 142 has a truncated shape, in the form of edge 143, so as to avoid stimulation of the femoral nerve.

A fourth positive electrode 146 is placed on the left obliques on the side of the abdomen above the iliac crest and a fifth return electrode 148 is placed proximate to the junction 714 of the left obliques 716 and the upper and lower portions 708 and 710 of the rectus abdominis. The fifth return electrode 148 is disposed between the fourth positive electrode 146 and third return electrode 144. By placing the return electrodes 144 and 148 adjacent to each other, the electrodes which stimulate the rectus abdominis are electrically isolated from the electrodes which stimulate the obliques thereby minimizing stimulation interaction. A sixth positive electrode 150 is placed on the right obliques on the side of the abdomen above the iliac crest and a seventh return electrode 152 is placed proximate to the junction 714 of the right obliques 716 and the upper and lower portions 708 and 710 of the rectus abdominis. The seventh return electrode 152 is disposed between the sixth positive electrode 150 and third return electrode 144 in order to again minimize stimulation interaction.

A voltage source such as an EMS machine provides the signals 134 and 138. An overall control box 121 can be attached to the covering 120, located nearby, or attached to an exercise device such as an ab roller exerciser. Individual adjustment controls 131, 132, and 133 determine the voltage delivered to first positive electrode 140, fourth and sixth positive electrodes 146 and 150, and second positive electrode 142, respectively. A master adjustment control 135 provides overall voltage control to the individual controls 131, 132, and 133. An adjustment control 136 simultaneously applies a first positive voltage 137 to fourth positive electrode 146 and a second positive voltage 138 to sixth positive electrode 150. As first positive voltage 137 increases, second positive voltage 138 decreases. And as first positive voltage 137 decreases, second positive voltage 138 increases.

Figure 15:
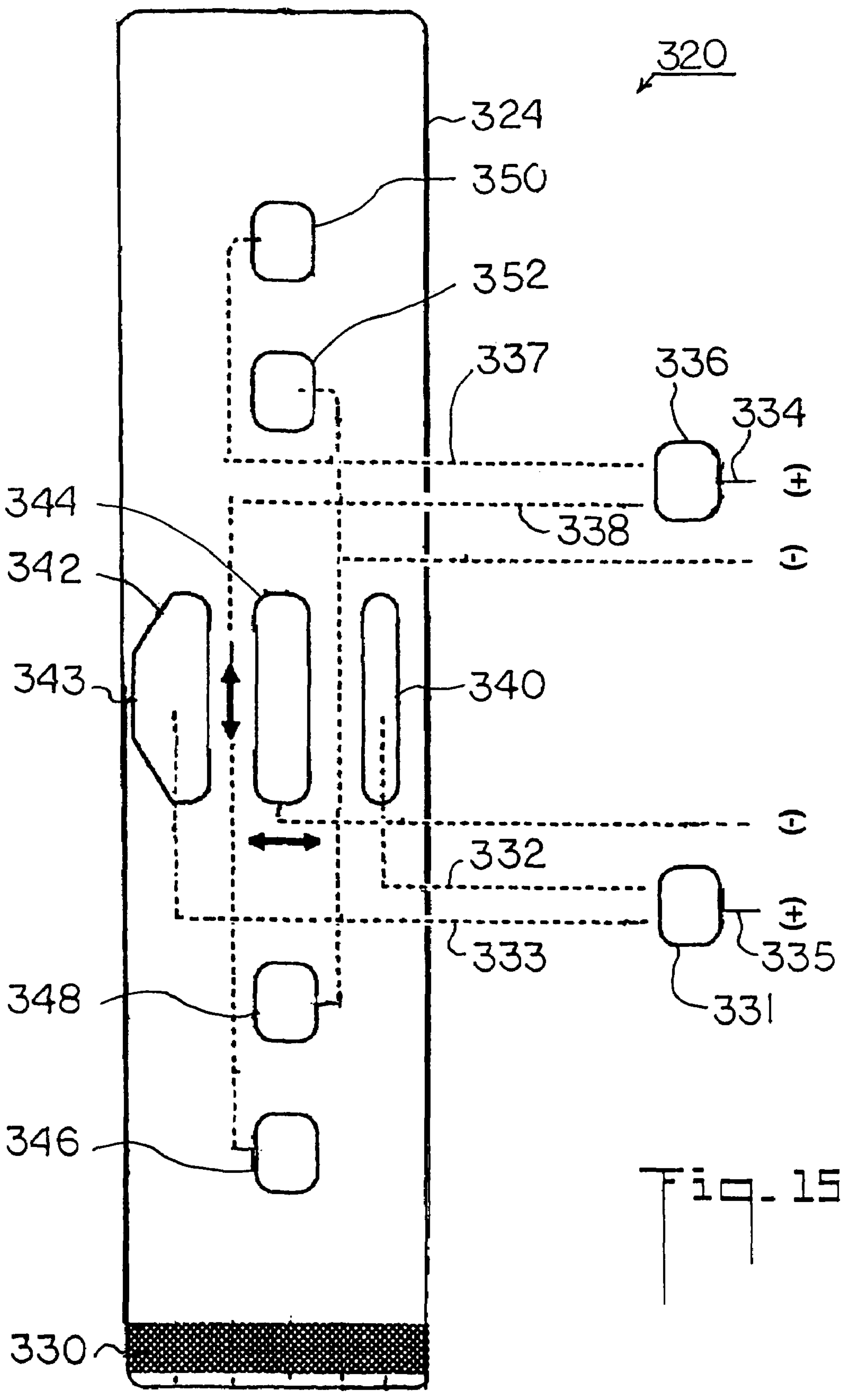
FIG. 15 is a top plan view of a second abdominal covering.

FIG. 15 illustrates a top plan view of the outside of a second abdominal covering 320 similar to abdominal covering 120 of FIG. 14 but having dual channels. Abdominal covering 320 includes a flexible covering or band 324, selectively positionable electrodes 346, 348, 350, and 352, and connector 330. Abdominal covering 320 includes a first positive electrode 340 which, when placed upon a patient, is proximate to the upper portion 708 of the rectus abdominis, a second positive electrode 342 which, when placed upon a patient, is proximate to the lower portion of the rectus abdominis, and a third negative return or common electrode 344 disposed between first 340 and second 342 positive electrodes in the umbilical region 712. Return electrode 344 provides a conduction path for both first positive electrode 340 and second positive electrode 342. It is noted that second positive electrode 342 has a truncated shape, in the form of edge 343, so as to avoid stimulation of the femoral nerve.

A fourth positive electrode 346 is placed on the left obliques on the side of the abdomen above the iliac crest and a fifth return electrode 348 is placed proximate to the junction 714 of the left obliques 716 and the upper and lower portions 708 and 710 of the rectus abdominis. The fifth return electrode 348 is disposed between the fourth positive electrode 346 and third return electrode 344. By placing the return electrodes 344 and 348 adjacent to each other, the electrodes which stimulate the rectus abdominis are electrically isolated from the electrodes which stimulate the obliques thereby minimizing stimulation interaction. A sixth positive electrode 350 is placed on the right obliques on the side of the abdomen above the iliac crest and a seventh return electrode 352 is placed proximate to the junction 714 of the right obliques 716 and the upper and lower portions 708 and 710 of the rectus abdominis. The seventh return electrode 352 is disposed between the sixth positive electrode 350 and third return electrode 344 in order to again minimize stimulation interaction.

The covering 320 has two channels. A first channel 335 for carrying a first electrical input channel signal provides stimulation and intensity control to the upper, mid, and lower rectus abdominis. A second channel 334 for carrying a second electrical input channel signal 334 provides stimulation and intensity control to the right and left obliques. Each channel operates independently from the other providing respective input to these muscle groups. A voltage source such as an EMS machine provides the first and second electrical input channel signals 335 and 334. The two diverging or balance controls 331, 336 are mounted on the covering or belt 320. Potentiometers may be used as the diverting devices. However, other diverting systems may also be used for example separate channels or multiple EMS units.

The first diverging control 331 distributes the first electrical input channel signal to the first channel 335 between the first positive electrode 340 placed over the upper rectus abdominis and the second positive electrode 342 placed over the lower rectus abdominis. The third electrode 344 located at the umbilicus acts as a return. This control facilitates the concentration of stimulation to either the upper or lower rectus abdominis. As the first positive voltage 332 to the first electrode 340 increases, the second positive voltage 333 to the second electrode 342 decreases. And as the first positive voltage decreases, the second positive voltage increases.

The second diverging control 336 distributes the second electrical input channel signal to the second channel 334 between the fourth positive electrode 346 over the right obliques and sixth positive electrode 350 over the left obliques. The fifth electrode 348 and sixth electrode 352 located along each junction of the obliques and rectus abdominis serve as returns. This control facilitates balance and equal stimulation of the right and left obliques. As the third positive voltage 337 to the sixth positive electrode 350 increases, the fourth positive voltage 338 to the seventh positive electrode 346 decreases. And as the third positive voltage decreases, the fourth positive voltage increases.

Figure 16:
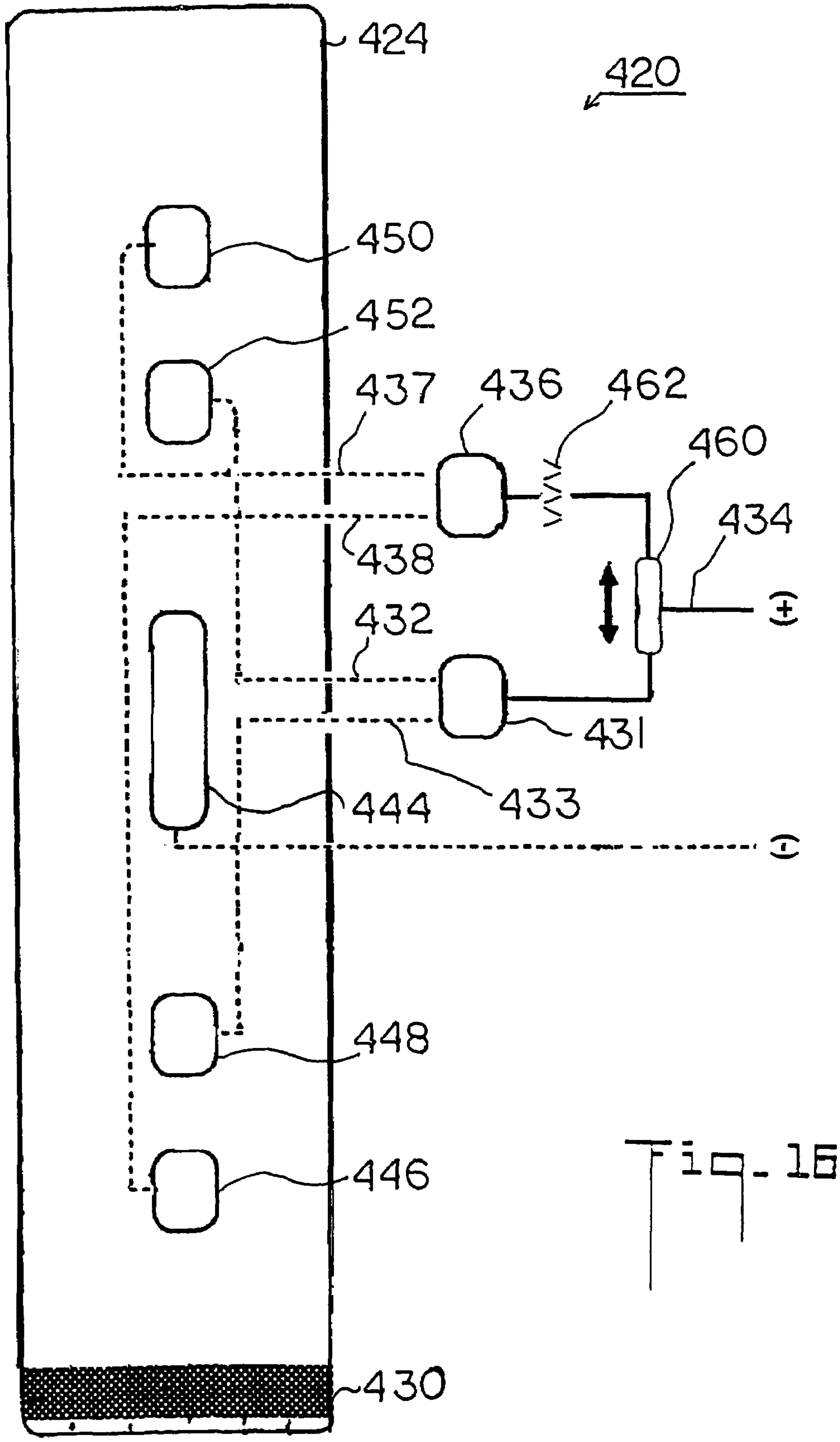
FIG. 16 is a top plan view of a third abdominal covering.

FIG. 16 illustrates a top plan view of the outside of a third abdominal covering 460 similar to abdominal covering 320 of FIG. 15 but having a single channel. Abdominal covering 420 includes a flexible covering or band 424, selectively positionable electrodes 444, 446, 448, 450, and 452, and connector 430. The control and versatility of the covering or belt is less than the dual channel covering or belt but it is more economical. The first return electrode 444 is placed on the rectus abdominis at the umbilical region. It is adjustable with respect to placement allowing the user to target any region between the umbillical and lower rectus abdominis. The second positive electrode 452 is placed at the junction of the rectus abdominis and left oblique muscles. The third positive electrode 448 is placed at the junction of the rectus abdominis and right oblique muscles. A first diverting device 431 controls the intensity balance between the second and third positive electrodes. The fourth positive electrode 450 is placed at the most lateral portion of the left obliques between the iliac crest and lower ribs. The fifth positive electrode 446 is placed at the most lateral portion of the right obliques between the iliac crest and lower ribs. First diverting device 431 simultaneously applies a first positive voltage 432 to second positive electrode 452 and a second positive voltage 433 to third positive electrode 448. As the first positive voltage 432 increases, the second positive voltage 433 decreases. And as the first positive voltage decreases, the second positive voltage increases. A second diverting device 436 controls the intensity balance between the fourth and fifth positive electrodes. Second diverting device 436 simultaneously applies a third positive voltage 437 to fourth positive electrode 450 and a fourth positive voltage 438 to fifth positive electrode 446. As the third positive voltage increases, the fourth positive voltage decreases. And as the third positive voltage decreases, the fourth positive voltage increases. A toggle switch 460 enables the user to alternatively stimulate the region between the rectus abdominis and medial obliques to target the anterior abdomen versus stimulating the region between the rectus abdominis and lateral obliques to target the lateral obliques. Generally, the lateral most aspects of the obliques are more responsive to electrical stimulation than the medial portions. A resistor 462 is therefore preferred to reduce the voltage to the lateral obliques when the toggle switch 460 is changed. This eliminates the sudden surge that may otherwise be experienced when the toggle switch is switched from the medial to lateral obliques.

Figure 17:
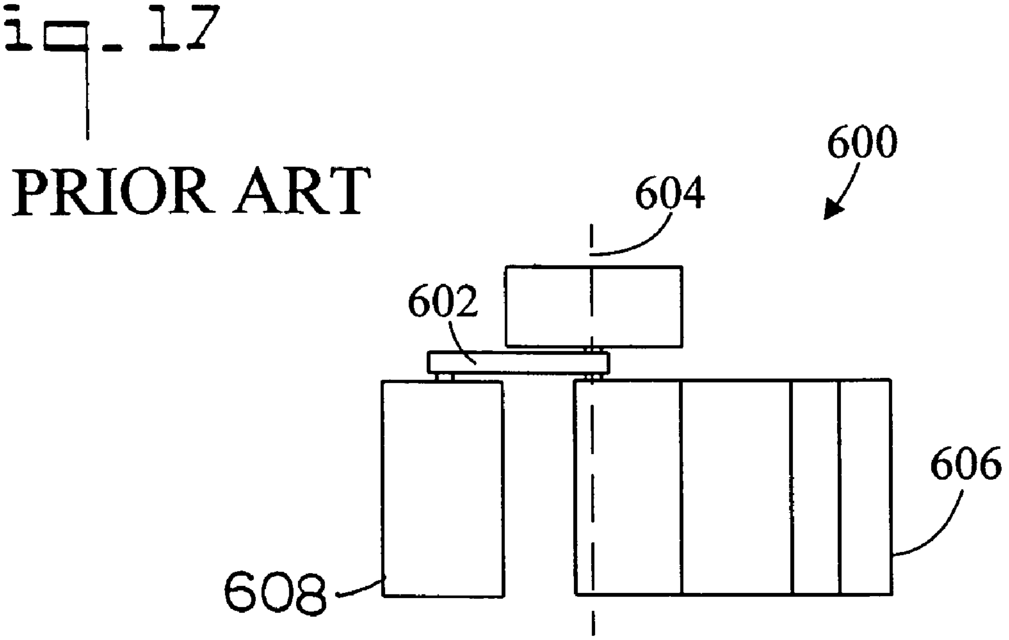
FIG. 17 is a top plan view of a second prior art exercise apparatus.
Figure 18:
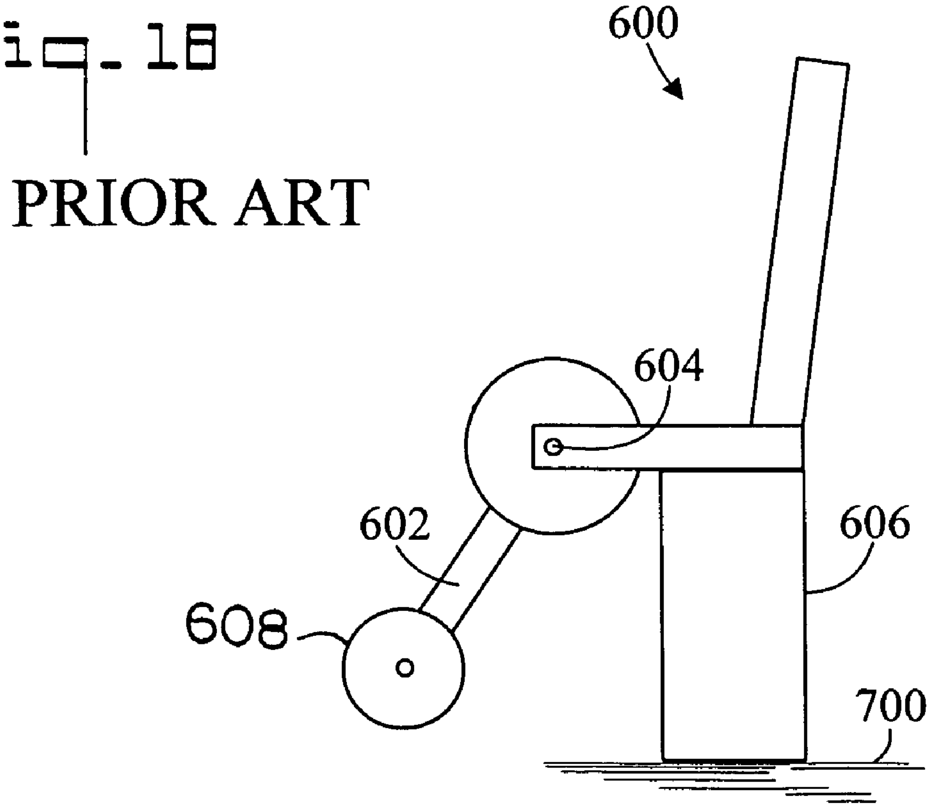
FIG. 18 is a side elevation view of the second prior art exercise apparatus.

FIGS. 17 and 18 illustrate top plan and side elevation views, respectively, of a second prior art exercise apparatus, generally designated as 600. In the shown embodiment, exercise apparatus 600 comprises a chair like device which is used to exercise the legs muscles of an exercising user. Exercise apparatus 600 includes a member 602 which is rotated about an axis 604 by the leg of the exercising user. A weight 608 provides rotational resistance. Member 602 rotates about base 606 which resides on a support surface 700.

Figure 19:
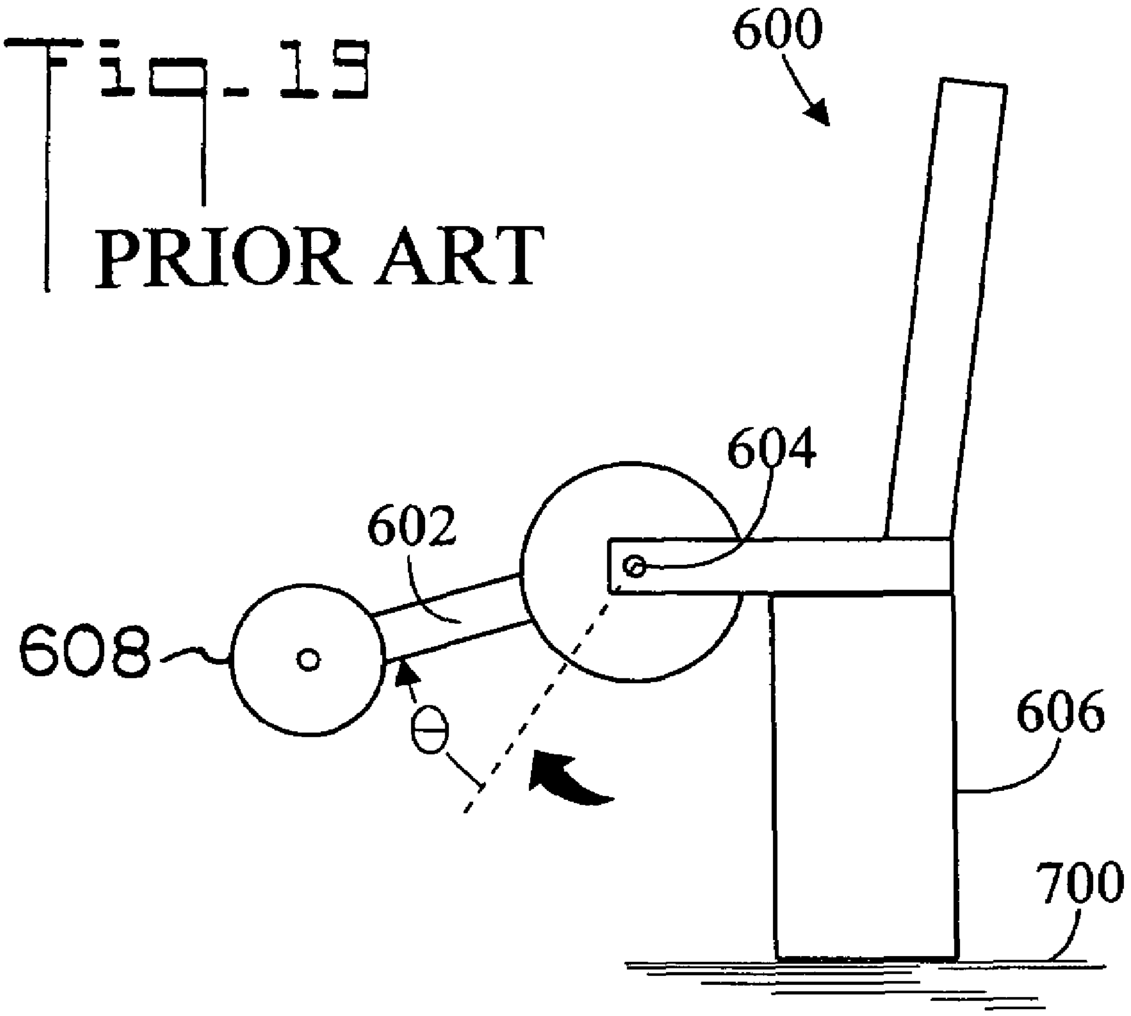
FIG. 19 is a side elevation view of the second prior art exercise apparatus rotated to a second position.

FIG. 19 is a side elevation view of prior art exercise apparatus 600 rotated through an angle θ to a second position.

Figure 20:
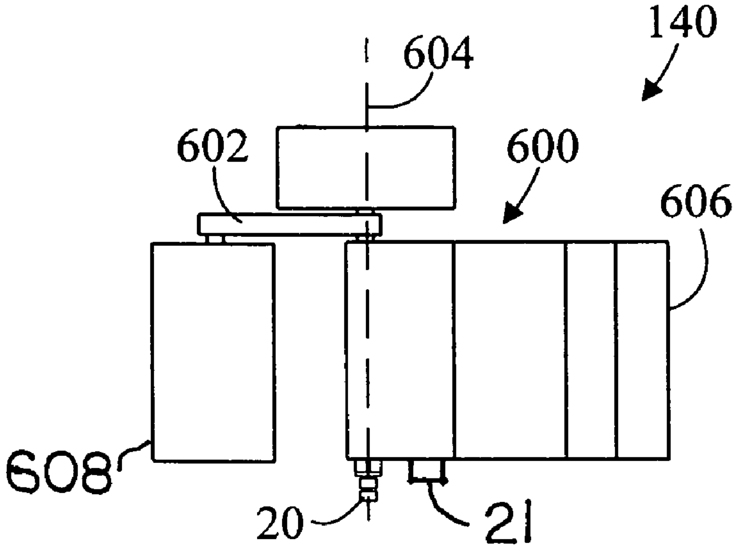
FIG. 20 is a top plan view of a second system for applying electro-muscle stimulation in accordance with the present invention.
Figure 21:
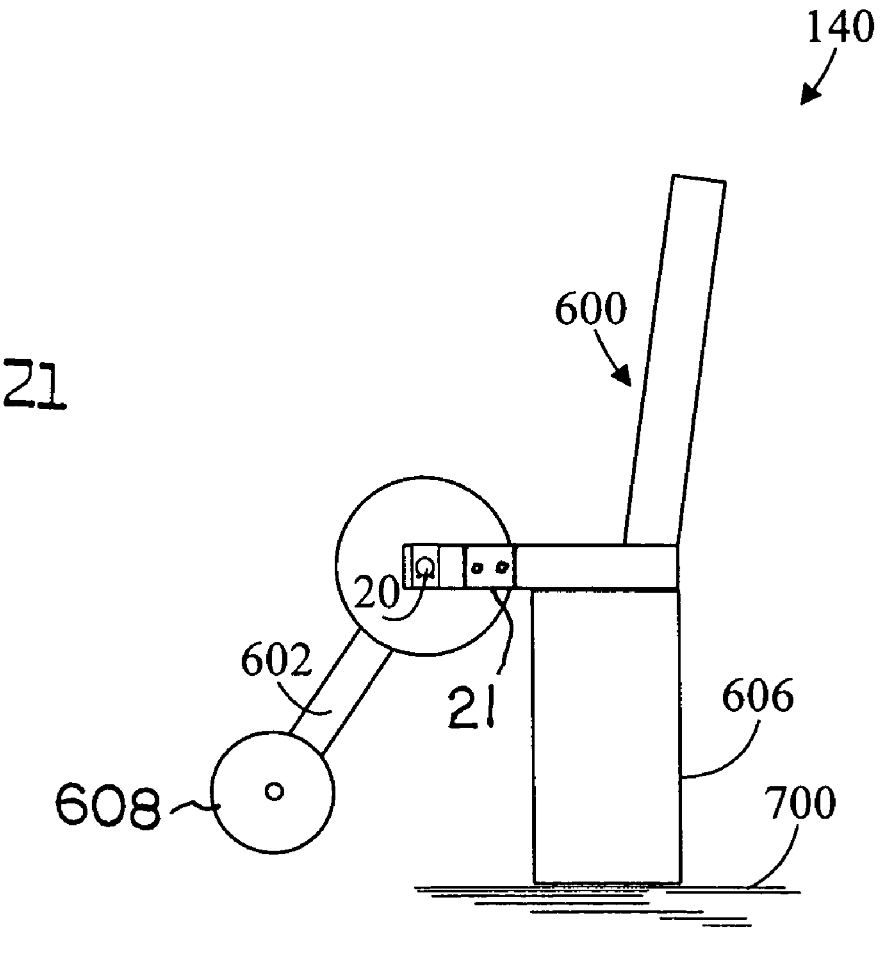
FIG. 21 is a side elevation view of the second system.

FIGS. 20 and 21 illustrate top plan and side elevation views, respectively, of a second system for applying electro-muscle stimulation in accordance with the present invention, generally designated as 140. System 140 includes exercise apparatus 600 having a member 602 which is rotatable about an axis 604 by an exercising user. A transducer 20 communicates with axis 604, so that as member 602 is rotated about axis 604, transducer 20 generates an output signal which is a function of an angular position of member 602.

Figure 22:
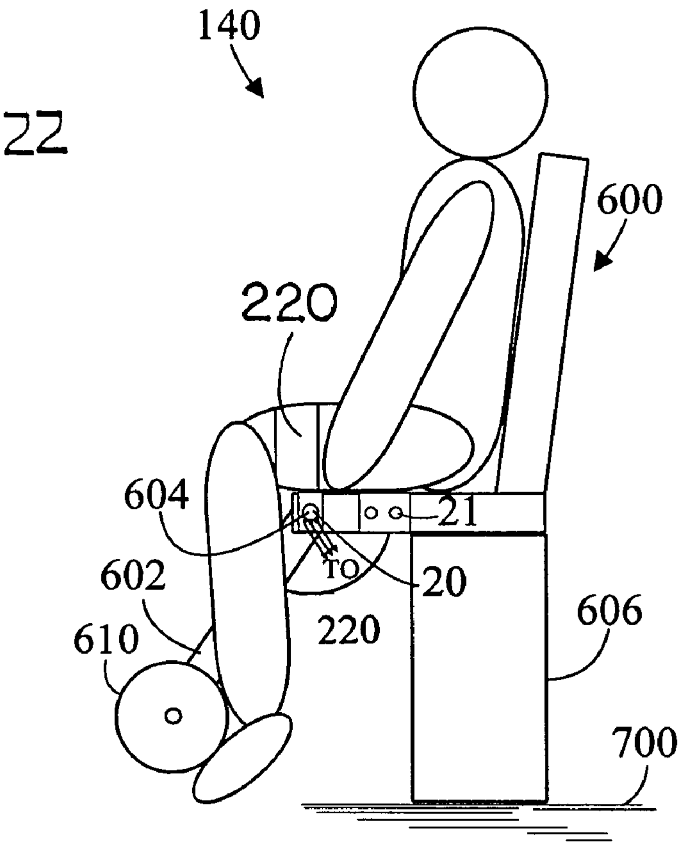
FIG. 22 is a side elevation view of the second system of the present invention being used by an exercising user in an initial position.
Figure 23:
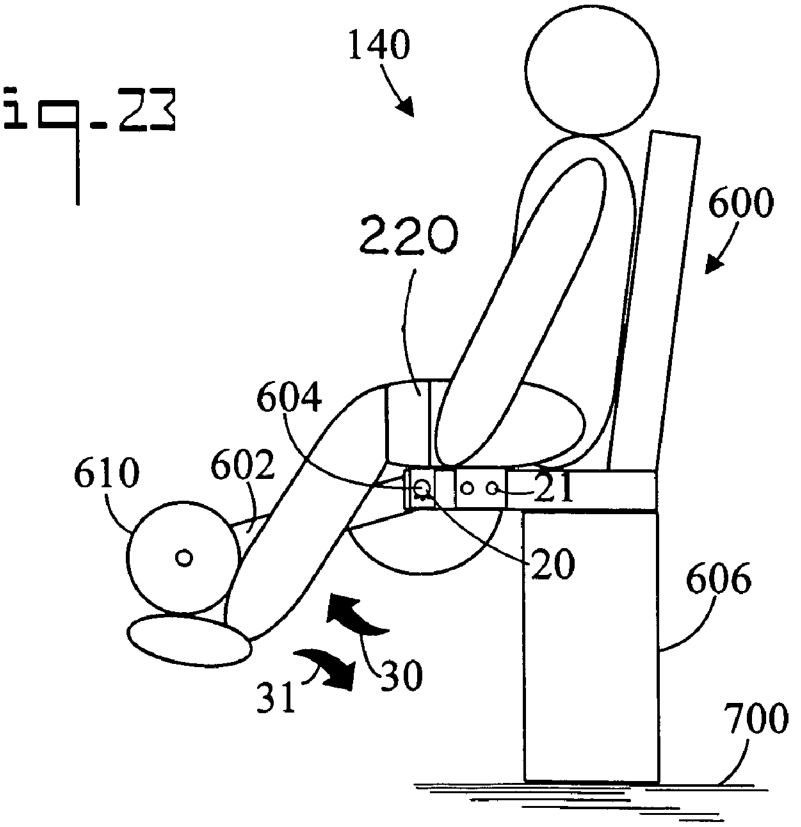
FIG. 23 is a side elevation view of the second system of the present invention rotated to a second position.

FIGS. 22 and 23 are side elevation views of system 140 being used by an exercising user. In FIG. 22 the leg of the user is initially at rest and hooked under a padded roller 610. In FIG. 23 the user has rotated member 602 to the shown position. An EMS covering 220 is disposed around the user's thigh. The output signal $V_\theta$ from transducer 20 is delivered to EMS covering 220. As the user rotates member 602 from the position of FIG. 22 in a first direction 30, output signal $V_\theta$ increases thereby causing increasing electro-muscle stimulation. Conversely, as the user rotates member 602 in an opposite second direction 31, output signal $V_\theta$ decreases thereby causing decreasing electro-muscle stimulation. It is noted that the output signal $V_\theta$ increases as the user is using his or her leg muscles to rotate member 602.

Applying increasing electro-muscle stimulation as the user is using his or her muscles, enhances the benefits of the exercise. Voltage level control 21 is conveniently located adjacent the hand of the user so that the intensity of the EMS can be adjusted during exercise without breaking the exercise rhythm.

Figure 24:
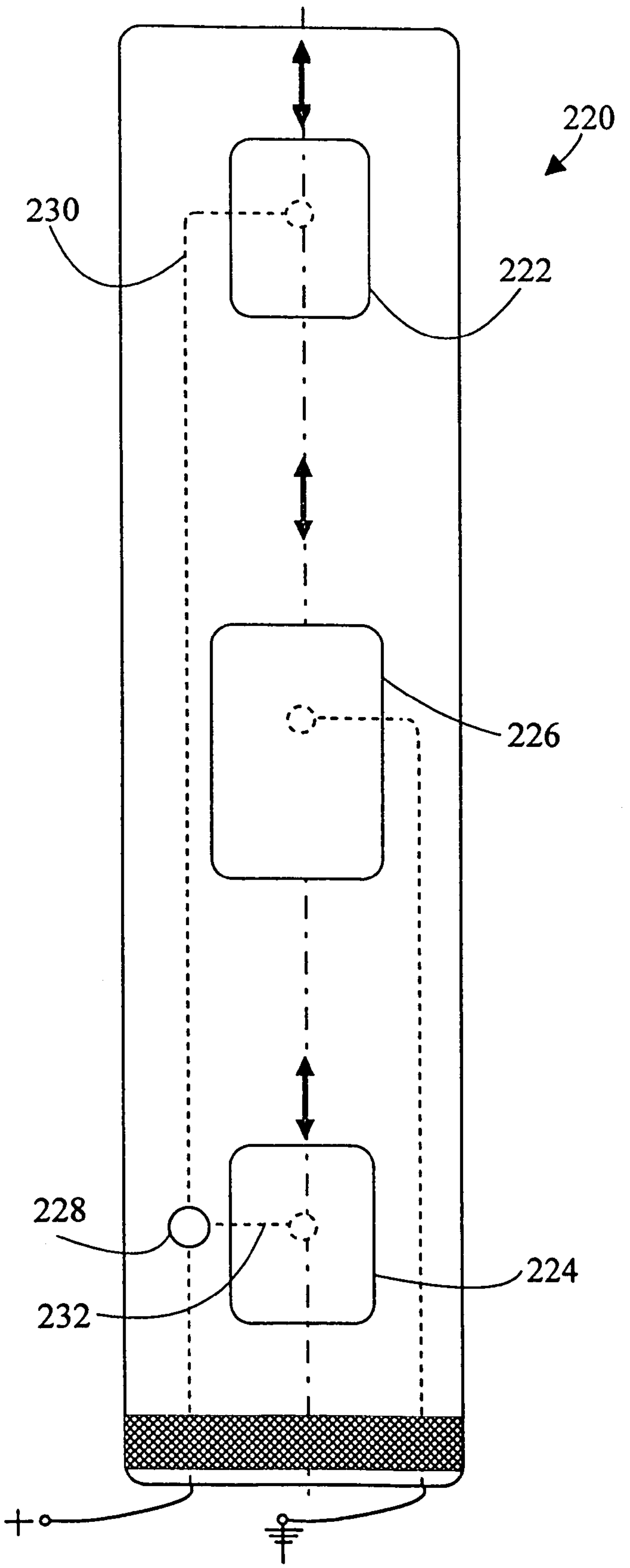
FIG. 24 is a top plan view of another covering.
Figure 25:
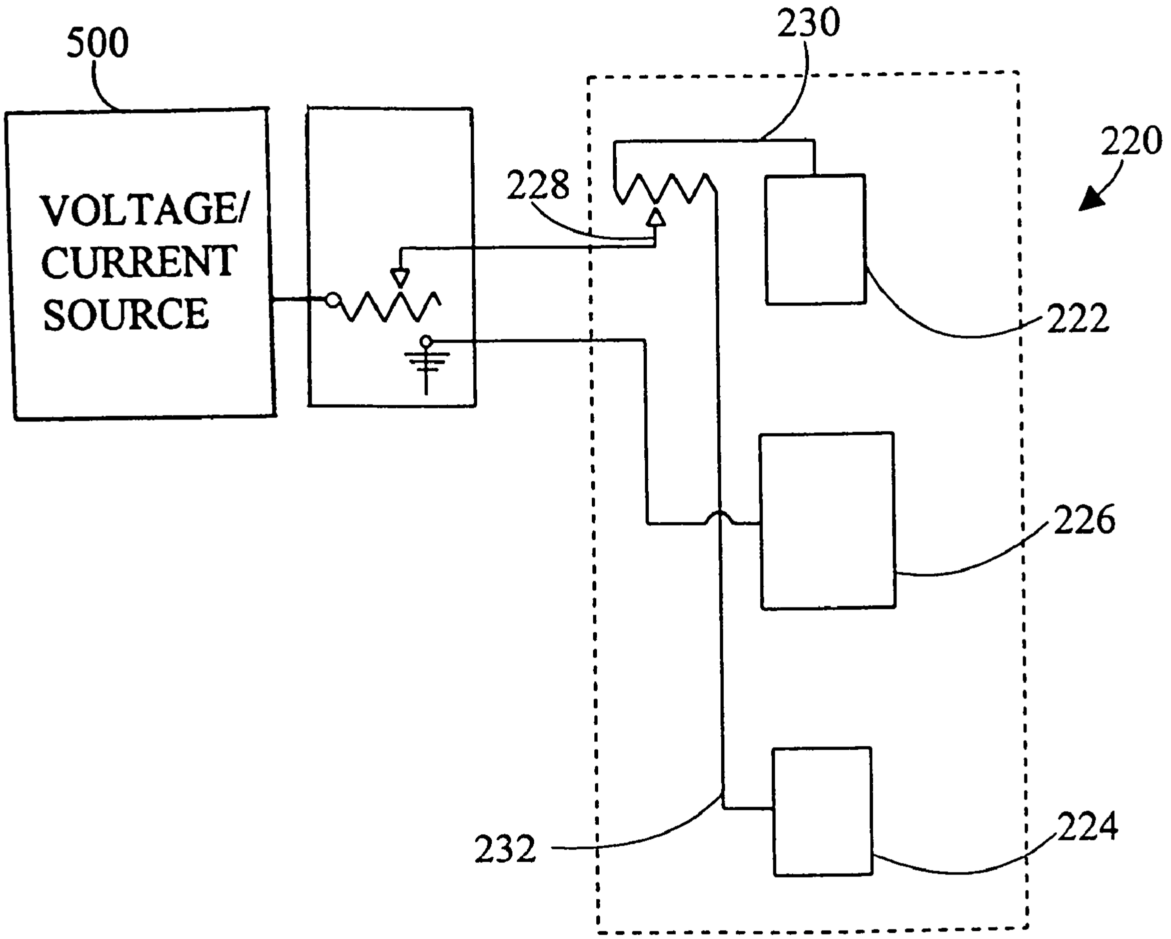
FIG. 25 is a schematic diagram of the covering of FIG. 24.

FIG. 24 is a top plan view of the covering 220 of FIGS. 22 and 23. FIG. 25 is a schematic diagram of the covering 220. Covering 220 includes a first positive electrode 222 and a second positive electrode 224. A return electrode 226 is disposed between first positive electrode 222 and second positive electrode 224. An adjustment control 228 simultaneously applies a first positive voltage 230 to first positive electrode 222 and a second positive voltage 232 to second positive electrode 224. As first positive voltage 230 increases, second positive voltage 232 decreases. And as first positive voltage 230 decreases, second positive voltage 232 increases. A voltage/current source 500 applies an electrical stimulation signal input. Covering 220 is designed for the application of traverse stimulation. In this application, a single covering 220 is utilized in which the positive and return electrodes are placed on the same covering. The central return electrode 226 is somewhat larger in surface area than the positive electrodes 222 and 224. This design allows the concentration of stimuli to the return electrode to become dispersed in order to dilute the intensity of the stimulation feed from both positive electrodes 222 and 224. It may be readily appreciated that the positive and return negative or ground electrodes may be reversed.

In terms of use, a method for applying electro-muscle stimulation, includes:

(a) providing a flexible electro-muscle stimulation covering 120 having a plurality of spaced apart electrodes 140, 142, 144, 146, 148, 150, and 152, said electrodes disposed in a pattern upon said flexible covering which matches a predetermined group of human muscles, so that when said flexible covering is placed upon a patient, said electrodes are proximate to the predetermined group of muscles, wherein said pattern matches predetermined groups of muscles, the muscles being the upper portion of the rectus abdominis, the lower portion of the rectus abdominis, the right obliques, and the left obliques.

(b) providing an exercise system 40 having:

an exercise apparatus 500 having a member 502 which is rotatable about an axis 504 by an exercising user;

a transducer 20 communicating with axis 504; and, so that as member 502 is rotated, transducer 20 generates an output signal $V_\theta$ which is a function of an angular position of member 502;

(c) providing an electro-muscle stimulation system (EMS) which delivers a voltage V1 (and/or V2) to transducer 20;

(d) providing electrical emphasis to certain regions over other regions within the muscle group;

(e) placing electro-muscle stimulation covering 550 upon the user;

(f) causing output signal $V_\theta$ to be delivered to electro-muscle stimulation covering 550;

(g) the user rotating member 502 in a first direction 30 thereby causing output signal $V_\theta$ to increase thereby causing increased electro-muscle stimulation to be applied to the user; and, (h) the user rotating member 502 in an opposite direction 31 thereby causing output signal $V_\theta$ to decrease thereby causing decreased electro-muscle stimulation to be applied to the user.

The method further including in step (b), transducer 20 being a potentiometer. The method further including in step (b), providing a plurality of tranducers 20. The method further including in step (c), a voltage level control 21 connected between electro-muscle stimulation system EMS and transducer 20; and, so that the voltage to the transducer may be adjusted.

In terms of use, an alternate method for applying electro-muscle stimulation, includes:

(a) providing an electro-muscle stimulation device having:

a flexible covering 320 having a plurality of spaced apart electrodes 340, 342, 344, 346, 348, 350, and 352;

the electrodes including:

a first positive electrode 340;

a second positive electrode 342; and, a return electrode 344 disposed between the first and second positive electrodes;

a voltage source 334 connected between the positive electrodes and the return electrode; and, an adjustment control 331 which simultaneously applies a first positive voltage 332 to the first positive electrode 340 and a second positive voltage 333 to the second positive electrode 342, so that as the first positive voltage increases, the second positive voltage decreases, and as the first positive voltage decreases, the second positive voltage increases;

(b) providing an exercise system 40 having:

an exercise apparatus 500 having a member 502 which is rotatable about an axis 504 by an exercising user;

a transducer 20 communicating with the axis 504; and, so that as the member 502 is rotated, the transducer 20 generates an output signal V1 which is a function of an angular position of the member 502;

(c) providing an electro-muscle stimulation system which delivers a voltage to the transducer;

(d) placing the electro-muscle stimulation covering 320 upon the user;

(e) causing the output signal V1 to be delivered to the electro-muscle stimulation covering 320;

(f) the user rotating the member 502 in a first direction 30 thereby causing the output signal to increase thereby causing increased electro-muscle stimulation to be applied to the user; and, (g) the user rotating the member 502 in an opposite second direction 31, thereby causing the output signal to decrease thereby causing decreased electro-muscle stimulation to be applied to the user.

The preferred embodiments of the invention described herein are exemplary and numerous modifications, variations, and rearrangements can be readily envisioned to achieve an equivalent result, all of which are intended to be embraced within the scope of the appended claims.

I claim:

1. A device for administering electro-muscle stimulation, comprising a flexible covering having a plurality of spaced apart electrodes, said electrodes disposed in a pattern upon said flexible covering which matches a predetermined group of human muscles, so that when said flexible covering is placed upon a user, said electrodes are proximate to the predetermined group of muscles, the muscles being the upper portion of the rectus abdominis, the lower portion of the rectus abdominis, the right obliques, and the left obliques, said electrodes proximate the upper and lower portions of the rectus abdominis connected together in a first channel to carry a first channel electrical input signal, the first channel configured to direct the first channel electrical input signal simultaneously to the electrodes proximate the upper and lower portions of the rectus abdominis, and said electrodes proximate the right and left obliques connected together in a second channel to carry a second channel electrical input signal, the second channel configured to direct the second channel electrical input signal simultaneously to the electrodes proximate the right and left obliques wherein the first channel and the second channel each have a diverging control having an input line, and output lines connected to their respective electrodes, wherein an increase in the voltage applied to one of the electrodes results in a decrease in voltage applied to the other electrode within each respective channel.

2. A device according to claim 1, wherein said first channel includes:

a first positive electrode for placement proximate the upper portion of the rectus abdominis;

a second positive electrode for placement proximate the lower portion of the rectus abdominis; and, a third return electrode disposed between said first and second positive electrodes.

3. A device according to claim 2, wherein said second channel includes:

a fourth positive electrode for placement on the right obliques on the side of the abdomen above the iliac crest;

a fifth return electrode for placement proximate the junction of the right obliques and the upper and lower portions of the rectus abdominis; and, said fifth return electrode disposed between said fourth positive electrode and said third return electrode.

4. A device according to claim 3, wherein said second channel further includes:

a sixth positive electrode for placement on the left obliques on the side of the abdomen above the iliac crest;

a seventh return electrode for placement proximate the junction of the left obliques and the upper and lower portions of the rectus abdominis; and, said seventh return electrode disposed between said sixth positive electrode and said third return electrode.

5. A device according to claim 4, wherein said diverging controls in said first and second channels include:

a first diverging control in said first channel for simultaneously applying a first positive voltage to said first positive electrode and a second positive voltage to said second positive electrode, so that as said first positive voltage increases, said second positive voltage decreases, and as said first positive voltage decreases, said second positive voltage increases; and, a second diverging control in said second channel for simultaneously applying a third positive voltage to said sixth positive electrode and a fourth positive voltage to said fourth positive electrode, so that as said third positive voltage increases, said fourth positive voltage decreases, and as said third positive voltage decreases, said fourth positive voltage increases.

6. A device for administering electro-muscle stimulation, comprising a flexible covering having a plurality of spaced apart electrodes, said electrodes disposed in a pattern upon said flexible covering which matches a predetermined group of human muscles, so that when said flexible covering is placed upon a user, said electrodes are proximate to the predetermined group of muscles, the muscles being the right and left obliques, including:

said plurality of spaced apart electrodes including:

a first return electrode for placement on the rectus abdominis at the umbilical region; a second positive electrode for placement on the medial obliques at the junction of the rectus abdominis and left oblique muscles;

a third positive electrode for placement on the medial obliques at the junction of the rectus abdominis and right oblique muscles;

a fourth positive electrode for placement on the lateral left obliques between the iliac crest and lower ribs; and, a fifth positive electrode for placement on the lateral right obliques between the iliac crest and lower ribs; and, a switch between said second and third positive electrodes and said fourth and fifth positive electrodes for enabling a user to alternatively stimulate the medial obliques or the lateral obliques.

7. A device according to claim 6, further including a resistor between said switch and said second and third positive electrodes for reducing the voltage applied to the lateral obliques when the switch is changed.

8. A device according to claim 6, further including:

a first diverting device between said second and third positive electrodes for simultaneously applying a first positive voltage to said second positive electrode and a second positive voltage to said third positive electrode, so that as said first positive voltage increase, said second positive voltage decreases, and as said first positive voltage decreases, said second positive voltage increases; and, a second diverting device between said fourth and fifth positive electrodes for simultaneously applying a third positive voltage to said fourth positive electrode and a fourth positive voltage to said fifth positive electrode, so that as said third positive voltage increases, said fourth positive voltage decreases, and as said third positive voltage decreases, said fourth positive voltage increases.

9. A device according to claim 8, further including a resistor between said switch and said first diverting device for reducing the voltage applied to the lateral obliques when the switch is changed.

10. A device for administering electro-muscle stimulation, comprising:

a flexible covering having a plurality of spaced apart electrodes, said electrodes disposed in a pattern upon said flexible covering which matches a predetermined group of human muscles, so that when said flexible covering is placed upon a user, said electrodes are proximate to the predetermined group of muscles, the muscles being the upper portion of the rectus abdominis, the lower portion of the rectus abdominis, the right obliques, and the left obliques, said electrodes proximate the upper and lower portions of the rectus abdominis connected together in a first channel to carry a first channel electrical input signal, the first channel configured to direct the first channel electrical input signal simultaneously to the electrodes proximate the upper and lower portions of the rectus abdominis, and said electrodes proximate the right and left obliques connected together in a second channel to carry a second channel electrical input signal, the second channel configured to direct the second channel electrical input signal simultaneously to the electrodes proximate the right and left obliques, wherein said first channel includes a first positive electrode for placement proximate the upper portion of the rectus abdominis, a second positive electrode for placement proximate the lower portion of the rectus abdominis, and a third return electrode disposed between said first and second positive electrodes, wherein said second channel includes a fourth positive electrode for placement on the right obliques on the side of the abdomen above the iliac crest, a fifth return electrode for placement proximate the junction of the right obliques and the upper and lower portions of the rectus abdominis, said fifth return electrode disposed between said fourth positive electrode and said third return electrode, the second channel further including a sixth positive electrode for placement on the left obliques on the side of the abdomen above the iliac crest, a seventh return electrode for placement proximate the junction of the left obliques and the upper and lower portions of the rectus abdominis, said seventh return electrode disposed between said sixth positive electrode and said third return electrode;

a first diverging control in said first channel for simultaneously applying a first positive voltage to said first positive electrode and a second positive voltage to said second positive electrode, so that as said first positive voltage increases, said second positive voltage decreases, and as said first positive voltage decreases, said second positive voltage increases; and, a second diverging control in said second channel for simultaneously applying a third positive voltage to said sixth positive electrode and a fourth positive voltage to said fourth positive electrode, so that as said third positive voltage increases, said fourth positive voltage decreases, and as said third positive voltage decreases, said fourth positive voltage increases.

* * * * *